US012594354B2

(12) United States Patent
Lary, Jr. et al.

(10) Patent No.: US 12,594,354 B2
(45) Date of Patent: Apr. 7, 2026

(54) COMPOSITIONS FOR VISUALIZATION OF CLEANING EFFICACY AND PRODUCT COVERAGE

(71) Applicants: Robert Yale Lary, Jr., Richmond, TX (US); Jeffrey Lee Kornacki, Madison, WI (US)

(72) Inventors: Robert Yale Lary, Jr., Richmond, TX (US); Jeffrey Lee Kornacki, Madison, WI (US)

( * ) Notice: Subject to any disclaimer, the term of this patent is extended or adjusted under 35 U.S.C. 154(b) by 0 days.

(21) Appl. No.: 14/636,729

(22) Filed: Mar. 3, 2015

(65) Prior Publication Data

US 2015/0174277 A1 Jun. 25, 2015

Related U.S. Application Data

(62) Division of application No. 13/662,029, filed on Oct. 26, 2012, now abandoned.

(60) Provisional application No. 61/630,805, filed on Oct. 26, 2011.

(51) Int. Cl.
| | |
|---|---|
| *A61L 2/18* | (2026.01) |
| *A23B 2/742* | (2025.01) |
| *A23B 2/754* | (2025.01) |
| *C09K 11/06* | (2006.01) |
| *C14C 1/08* | (2006.01) |

(52) U.S. Cl.
CPC ................ *A61L 2/18* (2013.01); *A23B 2/742* (2025.01); *A23B 2/754* (2025.01); *C09K 11/06* (2013.01); *C14C 1/08* (2013.01)

(58) Field of Classification Search
None
See application file for complete search history.

(56) References Cited

U.S. PATENT DOCUMENTS

| | | | |
|---|---|---|---|
| 2,449,274 A | | 9/1948 | Broll |
| 3,309,274 A | | 3/1967 | Brilliant |
| 4,662,403 A | * | 5/1987 | Hammer ................ B65D 65/38 |
| | | | 138/118.1 |
| 4,793,988 A | | 12/1988 | Casey et al. |
| 5,064,635 A | | 11/1991 | Casey |
| 5,156,766 A | * | 10/1992 | Behan ...................... A61K 8/06 |
| | | | 424/450 |
| 5,208,257 A | | 5/1993 | Kabara |
| 5,427,708 A | | 6/1995 | Stark |
| 5,443,987 A | | 8/1995 | DeCicco et al. |
| 5,658,798 A | | 8/1997 | Bertin et al. |
| 5,670,469 A | | 9/1997 | Dingus et al. |
| 5,894,620 A | | 4/1999 | Polaert et al. |
| 5,900,067 A | | 5/1999 | Jones |
| 6,033,705 A | | 3/2000 | Isaacs |
| 6,202,242 B1 | | 3/2001 | Salmon et al. |
| 6,331,515 B1 | | 12/2001 | Gambogi et al. |
| 6,419,902 B1 | | 7/2002 | Wright |

| | | | |
|---|---|---|---|
| 6,524,390 B1 | | 2/2003 | Jones |
| 6,616,451 B1 | | 9/2003 | Rizolu et al. |
| 6,638,978 B1 | | 10/2003 | Kabara |
| 6,769,911 B2 | | 8/2004 | Buchalla et al. |
| 7,053,029 B2 | | 5/2006 | MacDonald et al. |
| 7,060,136 B1 | | 6/2006 | Zeiher et al. |
| 7,247,330 B2 | | 7/2007 | Kuethe et al. |
| 7,425,900 B2 | | 9/2008 | Lynn et al. |
| 7,651,989 B2 | | 1/2010 | MacDonald et al. |
| 7,658,959 B2 | | 2/2010 | Koefod et al. |
| 7,989,780 B2 | | 8/2011 | Tokhtuev et al. |
| 2004/0018283 A1 | | 1/2004 | Hirschey et al. |
| 2005/0233919 A1 | | 10/2005 | Rich |
| 2006/0264346 A1 | | 11/2006 | Sullivan |
| 2006/0276541 A1 | | 12/2006 | Tautvydas et al. |
| 2008/0050398 A1 | | 2/2008 | Bockmuehl et al. |
| 2008/0187633 A1 | | 8/2008 | Cox |
| 2008/0255498 A1 | * | 10/2008 | Houle ................... A61C 17/02 |
| | | | 604/20 |

(Continued)

FOREIGN PATENT DOCUMENTS

| | | |
|---|---|---|
| WO | 92/06671 A1 | 4/1992 |
| WO | 96/029047 A1 | 9/1996 |

OTHER PUBLICATIONS

Pharmaceutical Manufacturing ( Clean in Place Systems Raise the Bar on Cleanliness Jul. 2004).*

Baroni, A., et al., "Antiviral Effects of Quinine Sulfate on HSV-1 HaCat Cells Infected: Analysis of the Molecular Mechanisms Involved," Journal of Dermatological Science, Sep. 2007; pp. 253-255, vol. 47, No. 3.

Kim, M. S., et al., "Hyperspectral Reflectance and Fluorescence Imaging System for Food Quality and Safety," Transactions of the ASAE, 2001, pp. 721-729, vol. 44, No. 3.

Lary, R. Y., et al., "Visual and Chemical Tissue Markers for Bovine Carcass Components," Journal of Animal Science, Apr. 1988, pp. 845-850, vol. 66, No. 4.

(Continued)

*Primary Examiner* — Nicole P Babson
(74) *Attorney, Agent, or Firm* — Lewis Rice LLC

(57) ABSTRACT

The invention relates to cleaning and food processing aide applications whereby unique compositions of GRAS or food additives were developed to assess the effectiveness of cleaning procedures at various stages of the processes and to assess the delivery and adherence of food processing aides. Employing such solutions to clean and/or sanitize processing equipment provides a method to evaluate and enhance the effectiveness of procedures used to remove the respective fluorescent detergents, sanitizers or organic residues from equipment or niches and reduce contamination. Similar compositions were developed for assessing processing aide food surface coverage, contact time and adherence. In addition, unique compositions were invented that increase processing aide coverage and adherence. Quantification of the presence or absence of the fluorescent GRAS or food additive compositions produces results for validation, monitoring and/or verification of food safety intervention procedures/processes.

12 Claims, 4 Drawing Sheets

(56) References Cited

U.S. PATENT DOCUMENTS

| | | |
|---|---|---|
| 2009/0237651 A1 | 9/2009 | Arndt et al. |
| 2011/0240057 A1 | 10/2011 | Lorch |
| 2013/0261037 A1 | 10/2013 | Fan et al. |

OTHER PUBLICATIONS

Lee, M.-K., et al., "Antimicrobial Activity of Glycerol Monolaurate and Organic Acids on the Survival of *Escherichia coli* O157:H7," International Journal of Food Sciences and Nutrition, 2001, pp. 6-9, vol. 6, No. 1.

Lieberman, S., et al., "A Review of Monolaurin and Lauric Acid: Natural Virucidal and Bactericidal Agents," Alternative & Complementary Therapies, Dec. 2006, pp. 310-314, vol. 12, No. 6.

Millipore, "Proven, Consistent Clean-In-Place Capability of Cogent (Tm) M TFF Systems," 2004, 4 pages.

Morey, A., et al., "Efficacy of Ultraviolet Light Exposure Against Survival of Listeria monocytogenes on Conveyor Belts," Foodborne Pathogens and Disease, Jun. 2010, pp. 737-740, vol. 7, No. 6.

Oh, D.-H., et al., "Enhanced Inhibition of Listeria monocytogenes by Glycerol Monolaurate with Organic Acids", Journal of Food Science, 1994, pp. 1258-1261, vol. 59, No. 6.

Poo-Prieto, R., et al., "Use of the Affinity/HPLC Method for Quantitative Estimation of Folic Acid in Enriched Cereal-Grain Products", The Journal of Nutrition, Dec. 2006, pp. 3079-3083, vol. 136, No. 12.

"Riboflavin test for low-germ or sterile process technologies Fluorescence test for examination of cleanability For food, aseptic, pharmacy and chemistry", VDMA, Dec. 2007, 10 pages, <https://www.vdma.org/documents/106036/1384898/Download1/4142532c-87ae-4a5e-855f-7f419289b577>.

Zhao et al., "Inactivation of *Salmonella* and *Escherichia coli* O157:H on Lettuce and Poultry Skin by Combinations of Levulinic Acid and Sodium Dodecyl Sulfate", Journal of Food Protection, vol. 72, No. 5, 2009, pp. 928-936.

Oleinick, N. L., "Basic Photosensitization," downloaded from <http://photobiology.info/Oleinick.html on Oct. 29, 2018, 12 pages.

Price, M., "A Role For Reactive Oxygen Species In Photodynamic Therapy," Wayne State University Dissertations, 2012, 95 pages, Paper 613.

\* cited by examiner

FIG. 3

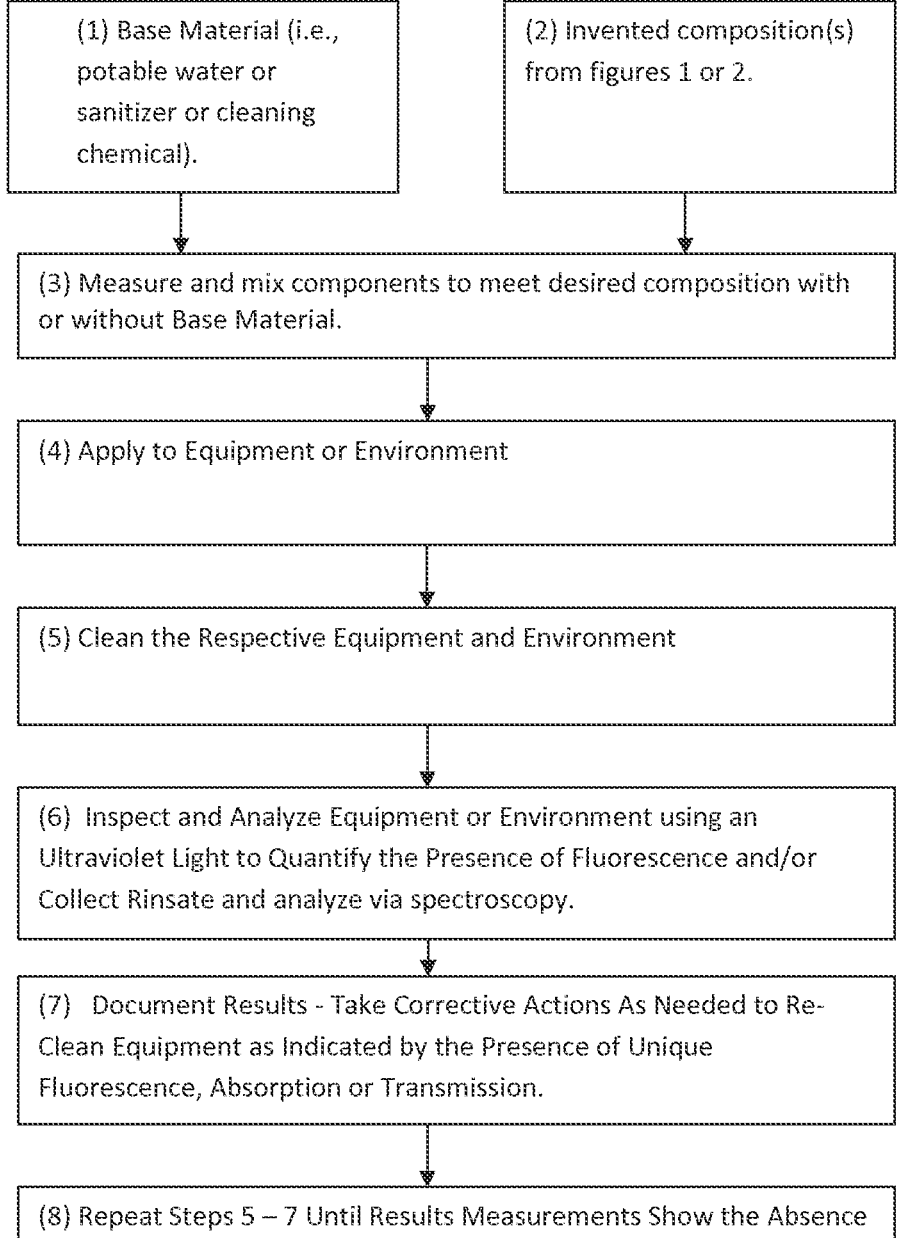

(1) Base Material (i.e., potable water or sanitizer or cleaning chemical).

(2) Invented composition(s) from figures 1 or 2.

(3) Measure and mix components to meet desired composition with or without Base Material.

(4) Apply to Equipment or Environment (5) Clean the Respective Equipment and Environment (6) Inspect and Analyze Equipment or Environment using an Ultraviolet Light to Quantify the Presence of Fluorescence and/or Collect Rinsate and analyze via spectroscopy.

(7) Document Results - Take Corrective Actions As Needed to Re-Clean Equipment as Indicated by the Presence of Unique Fluorescence, Absorption or Transmission.

(8) Repeat Steps 5 – 7 Until Results Measurements Show the Absence of Unique Fluorescence, Absorption or Transmission.

(9) Re-assess sanitation procedures and/or equipment/environment sanitary design as needed to improve hygienic conditions.

COMPOSITIONS FOR VISUALIZATION OF CLEANING EFFICACY AND PRODUCT COVERAGE

CROSS REFERENCE TO RELATED APPLICATIONS

This application is a divisional of U.S. patent application Ser. No. 13/662,029, filed on Oct. 26, 2012, which claims the benefit of U.S. Provisional Patent Application Ser. No. 61/630,805, filed on Oct. 26, 2011, the entire substance of which is incorporated herein by reference.

FIELD OF INVENTION

The present invention relates to enhanced cleaning and processing aid solutions whereby compositions of GRAS or food additive ingredients were invented to provide improved assessment tools, function and measurability.

BACKGROUND OF THE INVENTION

Food safety and quality professionals rely on validated processes to prevent illness. The processes covered in this invention include sanitation of equipment and application of processing aides to foods. Chemical and microbiological contamination caused by inadequate sanitary design of equipment or ineffective sanitation procedures are very serious risks in food, feed and pharmaceutical production. Very low levels of contamination can cause serious illness. For example allergic reactions can result from as low as 10 ppm of a chemical residue. Chemical residue can build up on surfaces or in niches and if not properly removed the compounds can cause cross contamination. *Listeria monocytogenes* (LM) can cause abortions and death at less than 100 organisms per gram. LM in food processing environments is transient or persistent. Transient organisms become persistent establishing colonies, increasing in numbers and developing biofilms that are impervious to chemical sanitizers. LM organisms are transported out of the niches by the motion of the equipment and or fluids, thus contaminating food contact surfaces and food. There are many niches in large scale processing equipment and food service kitchens, especially in equipment that was not designed or maintained with best in class sanitary design principles.

Poor equipment sanitary design conditions are easily missed by ineffective monitoring and verification of the cleaning and sanitation procedures. Typical cleaning monitoring activities involve daily visual pre-op inspection and periodic ATP, microbiological swabbing and chemical residue testing of small sampling points. Test kits are available for some, but not all food allergens, detergents and sanitizer residues. It is expected that no detergent levels remain after cleaning. However, a common problem associated with detergent residue testing is that detergent suppliers will not provide specific compositions and rapid test kits are not available which makes it difficult for the user to determine if they are completely removed.

The most common practice of visually evaluating the sanitary condition of equipment is limited when the objective is to clean to a microbiological and parts per million level of sensitivity. Microbiological swab sampling is limited in the area (i.e., square inches) tested, the cost per test and time for results. Limiting factors for ATP swab sampling include sample size and cost per test. Similarly, chemical residue tests are limited due the lack of rapid test kits, small sample size, time and cost associated with the analysis.

Traditional routine inspection methods are designed to evaluate a budgeted number of routine sample points instead of the entire processing line and all the potential niches, and are therefore subject to miss unhygienic conditions.

Food safety and quality professionals rely on validated processing aides to prevent food borne illness. Processing aides are defined by the Food and Drug Administration's (FDA) regulations (21 CFR 101.100 (a) (3) (ii)), as: a. Substances that are added to a food during the processing of such food but are removed in some manner from the food before it is packaged in its finished form, b. Substances that are added to a food during processing, are converted into constituents normally present in the food, and do not significantly increase the amount of the constituents naturally found in food and c. Substances that are added to a food for their technical or functional effect in the processing but are present in the finished food at insignificant levels and do not have any technical or functional effect in that food. Invalid food safety processing aides or interventions incorporated in food processing facilities pose the risk of causing food borne illness and public health incidents. For example, the infectious dose for *E. coli* O157:H7 which can cause hemolytic uremic syndrome is only 1 to 10 organisms per gram. Food regulations allow processors to incorporate certain pathogen interventions into their Food Safety Controls whereby delivery systems apply antimicrobial processing aids (FDA approved antimicrobial compounds) directly onto the food or it's precursors during production as defined in the Code of Federal Regulations Title 21, Part 101 Food Labeling, Subpart G and/or as listed in the United States Department of Agriculture (USDA) and the Food Safety Inspection Service (FSIS) Directive 7120.1 Safe and Suitable Ingredients Used in the Production of Meat, Poultry and Egg Products.

Antimicrobial intervention systems are developed in a laboratory environment. Initial intervention tests called "challenge studies" are designed and tested in controlled laboratory settings whereby food samples are inoculated with a known amount of microbiological target pathogenic organisms. After the target pathogens are allowed to attach to the target food or precursor samples, the inoculated samples are covered with the approved level of antimicrobial solution being tested or "challenged". After the samples have been covered for a set time, they are tested to determine if there is a reduction of the targeted microorganism. Once the intervention method to reduce the target pathogen is proven to be repeatable in the lab, the method is considered to be valid. Validation and verification of complete product coverage by the processing aide is essential in order for the interventions to be effective since dangerous pathogen contamination could be anywhere on the surface of a product at very low levels. For example, the infectious dose for *E. coli* O157:H7 (which can cause hemolytic uremic syndrome) is only 1 to 10 organisms per gram. And history has shown that facilities with scaled up processing aide delivery/intervention systems have been associated with food borne illnesses and product recalls.

Delivering antimicrobial solutions onto food so that adequate surface coverage is achieved in a processing plant is difficult. And quantifying adequate coverage is equally as difficult. Many times the product in which a processing aide is applied is conveyed on a belt or rails through a spray system. Often times the spray system is not accessible for observation of performance and at best, measuring coverage is subjective. The low concentration solutions are primarily water and many of the target foods are already wet from being rinsed with water prior to the processing aide/intervention application. It is difficult to distinguish between the intervention and rinse water when visually evaluating the surface of the treated product. Spray coverage and/or contact time can be inadequate from the onset of installation or can be diminished when spray nozzles malfunction or get plugged. Current methods to verify coverage and contact time during operation include observing the antimicrobial spray process and measuring the time required to pass through the system. At best it is difficult during normal line speeds to visually determine if the solution is covering the surface area per the intervention design objective. A method sometime used in the beef industry is to spread shaving cream on a condemned carcass at the end of the day and to evaluate it after is passes through the intervention system. Another method that has been used in the food industry is to wrap paper around the product, pass the product through the intervention spray and evaluate the post sprayed product for dry spots on the paper. Dyes have been added to the processing aide spray solution at the end of the production and determine the subsequent coverage after product has passed through the system. The product used for the test is discarded into inedible similar to the condemned carcass. However, use of such methods discovers areas not properly sprayed after production and since the measurement is not real time corrective actions during production are not possible.

The United States Department of Agriculture, Food Safety Inspection Service conducted a review of Food Safety Assessments and on site visits. The results of the review were published in FSIS Notice 17-1 on Mar. 2, 2012—Verification of Antimicrobial Intervention Coverage of Carcass or Product at Veal Slaughter and Beef Fabrication Establishments. A common deficiency was reported that antimicrobial or hot water interventions, such as sprays, did not reach all parts of carcasses and fabricated cuts. The USDA report went on to say that antimicrobial coverage-ensuring that the entire carcass or fabricated cut surfaces are treated—is necessary for the intervention to operate effectively and as intended. And as a result of incomplete coverage, interventions were likely less effective than intended, and this ineffectiveness may contribute to the production of contaminated products. If an establishment fails to implement its antimicrobial intervention so that its critical limits or prerequisite programs (including carcass/product coverage) are met, the Critical Control Point or prerequisite program(s) are not effectively controlling the hazard (9 CFR 417.2(c)(3)) and/or would call into question the adequacy of the Hazard Analysis of Critical Control Point system (9 CFR 417.6). Valid processing aide systems are also of great importance to the produce industry retail and food service demand for convenient and healthy fresh cut RTE fruits continues to increase. But fresh cut melons pose special food borne illness risks. Unlike other fruits, they are not acidic and the act of processing into fresh-cut increases the risk of pathogen contamination and growth once they are peeled or sliced. There have been 17 outbreaks linked to melons since 1985. Last summer cantaloupes were the cause of the most deadly food borne illness outbreak in 25 years. According to the CDC 30 people died and over 133 people were sickened. This summer an outbreak associated with cantaloupes caused two deaths and over 141 illnesses. Food processing plants need a practical and scientific method to validate and verify the coverage of processing aide delivery systems in their plants.

The current embodiments are focused on consumer protection related to raw and ready to eat foods, beverages, ingested or topical pharmaceuticals, animal feed and animal hides. The invention(s) in this present disclosure create food grade products made from novel mixtures of GRAS ingredients which may be used to prevent food borne illness associated with inadequate processing equipment cleaning procedures and inadequate antimicrobial intervention processing aide systems. The embodiment provides compositions that can be used to: 1) identify and measure insanitary conditions on or in processing equipment, 2) identify and measure processing equipment sanitary design flaws/niches, 3) identify and measure coverage of sanitizing solutions on equipment, 4) Identify and measure chemical residues on/or in processing equipment from cleaning and sanitizing compounds, 5) identify and measure processing aide coverage and contact time on a food surfaces. The embodiment also discloses a new composition for improving the adherence and coverage of food decontamination antimicrobials used in processing aide systems.

Use of food grade marking agents may be known. However, previous disclosures may not combine the specific GRAS ingredients or methodology for application and analysis as intended in this embodiment. Prior art and background information follows whereby the utility application to sanitation and processing equipment is presented first and the utility of direct food processing aides second. Cleaning Utility In 2008, the VDMA (German Process Plant and Equipment Association), Process Plant and Equipment Association, published an information sheet on a Riboflavin fluorescence test to examine cleanability. The individual performance of the test made it well-nigh impossible to make comparisons and gave repeatedly rise to questions therefore VDMA established a guideline including Riboflavin/water concentrations. In addition, the guideline suggests the use of Hydroxyethyl cellulose for increasing viscosity. VDMA states that the result of the test is a qualitative statement.

The current embodiment combines a unique group of GRAS or food grade ingredients that act synergistically to spread, penetrate and adhere to residue and niches on or in inanimate processing equipment. Food grade Riboflavin (21CFR73.450) and Quinine (21CFR172.575) are used to produce a novel dual fluorescence under the combination of short wave and long wave ultraviolet light. Folic acid may be safely added to food (21CFR172.345) and is included in the utility invention to provide unique absorbance characteristics. GRAS surfactant(s), emulsifier(s) and acidulates are added for improved performance with regard to penetration, adherence and coverage. The invention includes the previously mentioned components that can be combined with base material such as quaternary ammonium (quat) sanitizer/disinfectant or detergents. The addition of the invention additive solution improves the base material performance and provides a means for visual inspection as well as quantitative spectral absorption and fluorometric analysis.

For example, the composition of the invention includes multipurpose food additives Sodium Laurel Sulfate (21CFR172.822) and propylene glycol mono- and diesters of fats and fatty acids (CFR21172.856) which act as surface active agents and emulsifiers that reduce the surface tension to improve uniform solution coverage. The invention also includes a monoglyceride (Glyceryl Laurate—"Monolaurin") which is a GRAS surface-active agent and emulsifier (21CFR 184.1505) that improves spreading and penetration into equipment niches. Experiments by the authors of the current invention comparing Riboflavin alone or in combination with Sodium Lauryl Sulfate (SLS) or Glyceryl Laurate (Monolaurin) in solution have shown better penetration and adherence to organic residue in equipment niches when SLS or Monolaurin is combined in solution with Riboflavin. In addition to improved penetration, the current invention composition has been shown to reduce *Salmonella* and *Listeria monocytogenes*. Other studies have shown Monolaurin effective in inactivating gram positive bacteria, and a number of yeast, fungi and protozoa (Shari et. al. A Review of Monolaurin and Lauric Acid. Alternative & Complementary Therapies—December 2006, Antimicrobials in Food by P. Michael Davidson, John Nikolaos Sofos, Alfred Larry Branen Third Addition, 2005. The invention also incorporates organic acids such as citric acid to lower and stabilize the pH for optimal fluorescence and inhibition of bacteria in the composition during storage. Food grade Quinine is used in the invention because it fluoresces synergistically with Riboflavin via short wave ultraviolet light. Quinine also has antiviral properties (Baroni A et. al, Antiviral effects of quinine sulfate on HSV-1 HaCat cells infected: analysis of the molecular mechanisms involved. J Dermatology Sci. 2007 September; 47(3):253-5. Epub 2007 Jun. 27;

Although the current embodiment makes no claims associated with antimicrobial efficacy, a potential germicidal aspect of the current invention is found in the visual method of detection which includes short wave (~254 nm) ultraviolet light to excite Quinine sulfate so that it fluoresces in the visible (~460 nm) spectrum. Short wave ultraviolet light has been shown to have germicidal effects (Morey et. al. Efficacy of Ultraviolet Light Exposure Against Survival of *Listeria monocytogenes* on Conveyor Belts Food borne Pathogens and Disease. June 2010, 7(6):737-740). The current utility patent also differs from prior art because it provides both a visual qualitative evaluation of fluorescence under long wave and short wave ultraviolet light to detect the presence or absence of Riboflavin and Quinine; plus a quantitative spectroscopy method for analyzing the presence or absence of the vitamins Riboflavin and Folic Acid in the food grade invention thus indirectly measuring the presence or absence of the other components including the base material. Experiments by the authors using the invented compositions have shown that the method is sensitive to the 1 ppm level.

U.S. Pat. No. 2,449,274 (1948) and U.S. Pat. No. 2,449,274 related to self indicating bactericidal agents whereby fluorescein, uranine and fluorescent dyes in the phthalein class were added to quaternary ammonium in order to determine the reduced potency of the composition under ambient lighting. It was found that when various dyes of characteristic color and fluorescence are mixed with certain types of quaternary ammonium compounds possessing particular phenol coefficients, the characteristics of color and fluorescence are sharply modified. Further, when the phenol coefficient of the composition has become reduced to a predetermined value by contamination, a marked change in color and fluorescence occurs, thus providing the user with an unmistakable visual indication that the potency of the quaternary ammonia has been reduced.

The purpose of the current invention is not to determine reduced potency of sanitizers but to determine the presence or absence on food, feed or pharmaceutical equipment whereby many approved sanitizers including quaternary ammonia can be mixed with the fluorescent, penetrating GRAS additive composition to create a solution that can be applied to equipment, rinsed off and the equipment analyzed for the presence or absence of the invented solution. Discovery of presence on processing equipment sections and niches indicates that those areas were not properly cleaned and/or designed for ease of cleaning. In addition, the current invention allows for a quantitative method capable of detecting the presence of the fluorescent additive to 1 part per million. Thus, employment of the invented composition enables an inspector to determine if the sanitizer/food grade fluorescent additives have been adequately removed. This is very effective for use with Clean In Place (CIP) systems and is especially important to the pharmaceutical industry.

U.S. Pat. No. 5,064,635 (1991) provides a cleaning product with a disappearing pH sensitive dye that adds color when completely dispersed in the product and looses color due to neutralization from acidic CO2 in the air and on the surface on which it is sprayed. The dye thymolphthalein which is a pH indicator colored at alkaline pH and upon neutralization becomes colorless was disclosed as an example. U.S. Pat. No. 4,793,988 (1988) disclosed a germicide and dye composition whereby the dye disappears as the thin layer effects the germicidal activity of the disinfectant. The composition of the invention was rapidly drying, so that the dye disappears as well as the disinfecting composition leaving the surface dry. As with the previous invention the color was visible under ambient light and the pH of the composition must be alkaline for the dye to remain visible. In addition, both previously mentioned pH sensitive inventions must be packaged in airtight containers as exposure to ambient air neutralizes the composition and the color will disappear. Similarly, U.S. Pat. No. 6,331,515 (2001) discloses a pH sensitive alkaline liquid cleaning composition formed using FD&C Red 40 dye in the presence of sodium bisulfate which forms a reddish peach color when first made. At pH 9 the compound is color stable but at pH 5 to 7 the composition is not color stable and a color change from reddish peach to yellow occurs. The current embodiment does not utilize a color change for detection but instead utilizes fluorescence and unique spectral properties to determine the presence or absence of fluorescent food grade additives that are mixed into approved base materials.

U.S. Pat. No. 5,670,469 (1997) discloses compositions containing a visible coloring agent, such as a pigment or dye (preferred T-15 Blaze Orange™) together with a polymer (example polyethylene glycol or polypropylene glycol) or hydroxylate aliphate alcohol (example glycerol, sulfated eythoxylate alcohol, turpene, butane diol, hexane di and triol) a surfactant (such as d-limonene or carboxymethylcellulose). The composition could contain a biocide and/or water. The composition has a characteristic thick and sticky quality that makes it moderately hard to wash off which is important for monitoring cleaning thoroughness. The detectable agent is readily visible under normal white light and provides a technique for monitoring disturbed and undisturbed areas on a surface. U.S. Pat. No. 5,427,708 (1995) discloses glow in the dark liquid soap using chemiluminescent, phosphorous or other known active glow in the dark material. By "active" is meant that it glows in the dark before being dispersed and is not latent material which requires an initiator to be activated. The current invention is similar in that one of the purposes is to identify sections surfaces that were not thoroughly cleaned. However, the current invention is composed of 100% GRAS ingredients including surfactants, emulsifying agents, acidifiers and fluorescent vitamins that facilitate the tracer penetration to determine the effectiveness of cleaning. Moreover, the current invention is not visible under normal white light nor will it glow in the dark without an initiator (i.e., excitation via short wave short wave and long wave ultraviolet light). Finally, the current embodiment is not intended as a novel aspect to shampoos, bars or cakes of soap, but to detect niches in processing equipment that could harbor bacteria or chemical residues.

U.S. Pat. No. 3,309,274 (1967) provides solutions, pastes and powders that contain a normally invisible constituent under ambient light that fluoresces and becomes visible when activated by the appropriate light source. The constituent when combined in mouthwash, toothpaste or chewing gums, crackers and comparable otherwise edible foods when applied to oral cavities having a disease causing foreign matter, cause the foreign material in the oral cavity to glow and become visible when exposed to an appropriate light source. The embodiment disclosed fluorescent F,D&C Red #3, Green #8, Red #29, Red #22, Red #28, Yellow #7 and Yellow #8. The current invention uses food grade Riboflavin and Folic Acid with Riboflavin as the primary fluorescent constituent that fluoresces in the visible spectrum when excited by ultraviolet light (365 nm). Folic Acid emits energy (365 nm) when excited by short wave ultraviolet light (290 nm) therefore when excited can act as an additional 365 nm energy source to excite Riboflavin fluorescence. The current invention utilizes the combination of vitamins to achieve fluorescence under long and short wave ultraviolet light and does not use any of the fluorescent constituents disclosed in the referenced patent. The current invention also incorporates surfactants, emulsifiers and acidifiers to better penetrate, spread and maintain hygienic conditions.

Numerous methods for adding dyes, pigments and fluorescent or phosphorescent compounds to hand washing mediums to evaluate the effectiveness of a person's hand washing techniques have been noted and described in U.S. Pat. No. 6,524,390 (2003), U.S. Pat. No. 0,237,651 (2009), U.S. Pat. No. 5,900,067 (1999), U.S. Pat. No. 0,264,346 (2006), U.S. Pat. No. 7,053,029 (2006), U.S. Pat. No. 7,425,900 (2008) and U.S. Pat. No. 7,651,989 (2010). Methods for evaluating the effectiveness include combining coloring agents; moving the person's hands into contact with one another so to spread the hand washing medium over both hands; scrubbing the hands with the compound(s) either to release color agents or until the color of the hand wash medium changes; rinsing the hands; evaluating presence or absence of released coloring agent(s) to determine the presence on the person's hands indicating an unwashed portion of the hands. Although these patents disclose methods to determine unclean hands after a marker has been applied they do not utilize the unique combination of GRAS or food additive fluorescent vitamins, surfactants, emulsifiers and acidifiers to provide a penetrating marking composition.

Processing Aide Utility

As previously stated, FDA and USDA allows processing aides to be applied to foods whereby certain antimicrobial intervention solutions are sprayed directly onto food without requirements for labeling as long as the safe and suitable "processing aide" compounds do not have a lasting effect, are used within maximum limits and do not add more than 0.5% weight gain to the food it is applied to. Safe and suitable FDA approved additives may be used in excess of the "processing aide" allowances as long as they are included on the food product ingredient statement. Antimicrobial processing aides are widely used in the meat harvest and processing industry to control pathogens. The Food Safety and Inspection Service (FSIS) have issued Docket No. FSIS-2009-0019 HACCP Systems Validation in the Federal Register/Vol. 77, No. 90/Wednesday, May 9, 2012 to clarify its requirements for validation by an official establishment of its Hazard Analysis Critical Control Point (HACCP) system, that is, validation of both the critical control points (CCPs) in the HACCP plan and any interventions or processes used to support decisions in the hazard analysis. Processing aide intervention systems have been instrumental in reducing the incident rate of pathogens on foods. Such processes are included as pre-requisite programs and critical control points in food processing plants. However, there is a need for quantifiable methods for in plant determination of adequate target food surface coverage and adherence. It is disruptive and costly to test processing aide delivery system performance in the actual food plant where the equipment is intended to be used. Testing typically occurs after or before production and includes non food grade dyes or fluorescent compounds that contaminate the food samples and food processing equipment. In a food plant environment the performance of the intervention cannot be validated or verified by inoculating food samples with pathogenic organisms, treating the food through the intervention system and then measuring the reduction of pathogenic organisms. Introducing known pathogens in a food plant is not acceptable.

Testing/validating a scaled up delivery system design using microorganism challenge studies or liquid dyes can be performed in a location other than the actual food plant to prevent contamination. And food plants can perform small tests at the end of the day using dyes and discard the tested food into inedible and incorporate special sanitation procedures to decontaminate the food processing equipment prior to running product for sale. However, the best method is to validate the system in the actual operating conditions and to verify performance using statistical process control sampling frequencies during production.

Regulatory approved antimicrobial solutions are difficult to visually measure after they have been applied to food products. Many of the foods are wet from being rinsed and or washed with water prior to application of the antimicrobial solution(s). And since most of the antimicrobial compounds are mixed into water at very low concentrations, the solution on the treated food is clear like water and not distinguishable. Food grade dyes could be added to the antimicrobial solutions so that the application on or into the food could be visually evaluated. However, dyes change the visual appearance of the food product and in many applications this outcome is not desired. The most widely used method in the industry to assure proper coverage is to visually observe the spraying system in action. Most intervention spray cabinets are not accessible during production which adds risk that malfunctions could occur un-noticed.

Food processing plants need a practical and scientific method to validate and verify the adequacy of effective antimicrobial delivery system coverage in their plants. The method should be food grade, quantifiable and not alter the visual appearance of the finished product.

Prior art for measuring the coverage of a direct food contact processing aid/antimicrobial intervention is limited. Lary (co-author of current invention) et al 1988, showed Riboflavin to be an effective non-toxin and quantifiable beef carcass marker. Live cattle were injected subcutaneously with Riboflavin suspended in distilled water and the respective carcasses were evaluated after harvest. All injection sites evaluated on pre and post chilled carcasses under long-wave ultraviolet light showed intense fluorescence and were positively identifiable ($p<0.001$). While the same sites when evaluated under visible light were not distinguishable from other areas of the carcass. See Lary et. al, Visual and Chemical Tissue Markers for Bovine Carcass *J Anim Sci* 1988. 66:845-850.

The current invention includes Riboflavin as a fluorescent component. However, the difference in the current disclosure from prior art is that the current embodiment is composed of Riboflavin plus additional GRAS or food additive ingredients that increase the coverage, penetration and adherence of the antimicrobial processing aides that can be applied onto the surfaces of many different types of food including meat, poultry, fruits and vegetables. In addition, acidifiers such as Citric Acid are also added to the embodiment containing Riboflavin in order to stabilize the pH, to prevent quenching of fluorescence under ultraviolet light and to prevent microbial outgrowth in the premixed composition. Although the original purpose of the GRAS or food additive ingredient fluorescent tracer composition of the current invention was to measure coverage or lack thereof after application of a processing aide in order to improve the effectiveness of the delivery system; during experimentation, the authors of the current embodiment discovered that coverage and adherence of antimicrobial processing aides was greatly improved by altering the composition of the various processing aide solutions to include a wetting agent selected from a group of cationic, anionic and nonionic surfactants and an emulsifier selected from a group of mono and diglycerides mixed into a carrier selected from a group of water, propylene glycol or mixtures thereof. This discovery was made possible by the fluorescent aspect of the embodiment whereby the physical interaction of the antimicrobial solutions with the surfaces of the food samples was carefully evaluated under ultraviolet light. Repeated observations by the authors showed the discovery to be consistent. It should be noted that the authors could not visibly determine differences between processing aide performance with regard to coverage or adherence on food surfaces with or without a wetting agent or emulsifier when samples were evaluated without the fluorescent component(s) of the invention.

The purpose of the prior art was to inject Riboflavin and water subcutaneously into diseased animals that were condemned from entering the food supply so that illegal practices could be prosecuted in the event carcasses from the injected animals were discovered inside manufacturing facility or in distribution. As mentioned, the current embodiment is intended for food to be consumed and it utilizes a composition of other GRAS or food additive ingredients to enhance coverage and adherence in addition to fluorescence traceability. Moreover, the current embodiment composition may include low levels of Folic Acid and Quinine with Riboflavin to synergize fluorescence and to provide a unique spectral fingerprint. Rosalia Po' o-Prieto et. al, 0022-3166/ 06-2006 American Society for Nutrition showed that Folic Acid excited by ultraviolet (UV) light in the midrange spectra (290 nm) emits long wave (365 nm) UV light. Riboflavin is known to fluoresce when excited by long wave UV light with peak fluorescence at 365 nm (Wikipedia 2012).

U.S. Pat. No. 7,247,330 (2007) and U.S. Pat. No. 0,018, 283 (2004) provides a method for controlling pathogenic contamination on ready to eat (RTE) processed meats using steam combined with an antimicrobial spray. The method includes introducing the marking agent into the package cavity and vacuum sealing 4 to 10 wieners in the package such that the package cavity and package shrinks around the wieners and the marking agent is used to determine if the antimicrobial was uniformly dispersed over the food surface. A non specific fluorescent compound is mentioned as a potential indirect antimicrobial marking agent especially adapted for vacuum packaged processed meats.

The current embodiment methodology does not spray the antimicrobial into the package expecting the vacuum system to spread the solution over the product surface. Instead the current invention is a composition that is applied directly onto the target food and includes a wetting agent and an emulsifier to enhance coverage and adherence of the antimicrobial and/or fluorescent component(s) in solution. Coverage of the invention solution is measured by visually evaluating the treated food(s) for fluorescence under long and short wave UV light.

U.S. Pat. No. 5,658,798 (1997) provided fluorescent material selected from mixtures consisting of naphthalene sulfonate salt, mono- and dimethyl naphthalene sulfonate salt, 1,5 naphthalene disulfonate salt, 2-naphthalene sulfonate salt, riboflavin, tyrosine, beta carotene, 1-tryptophan, sodium lignosulfonate, sodium humate, fluorescene, 1-dopa for use in boiler make up water systems to detect re-circulated water impurities caused by product components contaminating the water stream used for processing food. The fluorescing constituent was proposed to be a fluorescing impurity of a food product, or the food product itself if such naturally fluoresces in a food processing stream within food processing equipment which contains circulating water selected from the group consisting of boilers, chillers, evaporators, pasteurizers and thermal processors. The current embodiment is not intended to detect impurities in the water of a food processing stream.

Much research has been documented on the antimicrobial properties of formulas containing Monolaurin, Sodium Lauryl Sulfate and organic acids. U.S. Pat. No. 6,638,978 (2003) discloses the antimicrobial properties of combining fatty acids with various components including propylene glycol and lactic acid. U.S. Pat. No. 5,208,257 (1993) discloses the antimicrobial properties of compositions containing mono glycerides (a glycerol ester mono ester of lauric acid) and a surfactant (Sodium Lauryl Sulfate) while U.S. Pat. No. 7,658,959 (2010) discloses the antimicrobial properties of compositions containing Sodium Lauryl Sulfate. The current embodiment makes no claims regarding antimicrobial utility of the compositions invented herein. The utility of the current invention is to combine GRAS emulsifiers, fluorescent vitamins and acidifier additives with FDA and FSIS approved antimicrobial base materials in order to create an improved antimicrobial intervention solution that covers, adheres and can be measured on the target food after it has been directly applied in order to improve and determine the adequacy of the food surface coverage and processing aide contact adherence. Measurement of coverage and adherence adequacy is accomplished without disruption to the operations whereby the treated food(s) associated with the food grade intervention system can be visually evaluated under long and short wave ultraviolet light to measure the presence or absence of unique fluorescence caused by the fluorescent additive invention combined into the base antimicrobial solution. Experiments by the authors using the disclosed composition including a wetting agent selected from a group of cationic, anionic and nonionic surfactants; b) an acidulant selected from a group of organic acids and mixtures thereof; c) an emulsifier selected from a group of mono and diglycerides; d) fluorescent tracers selected from food additive ingredients; and e) a carrier selected from a group of water, propylene glycol or mixtures thereof; wherein the composition includes only materials that are considered GRAS or food additive ingredients and the composition is adapted to remain on the food, have shown that processing aide coverage and adherence improved. Therefore, the current embodiment provides an improved processing aide composition to the food industry with a practical method for validating or verifying food safety antimicrobial intervention system performance with regard to surface coverage and adherence.

SUMMARY OF INVENTION

The present inventions create compositions that provide products that can be used as tools to improve hygienic sanitation conditions of processing equipment and to improve antimicrobial processing aide performance as applicable in the food, feed, beverage, processing and service industry. Compositions of GRAS or food additive ingredients were developed that when mixed into food grade base materials independently or in combination create compositions resulting in improved solutions that comply with the Food and Drug Administration, the United States Department of Agriculture Food Safety Inspection Service and the Environmental Protective Agency regulations associated with indirect food contact surface and direct food contact application.

The general idea of the invention is that a unique food grade additive packet has been developed composed of a synergistic combination of food grade additives with composition properties for improving the functionality of base materials as related to coverage, penetration, adherence, stability and measurement. The food grade additive packet is composed of a wetting agent selected from a group of cationic, anionic and nonionic surfactants; b) an acidulant selected from a group of organic acids and mixtures thereof; c) an emulsifier selected from a group of mono and diglycerides; d) fluorescent tracers selected from food additive ingredients; and e) a carrier selected from a group of water, propylene glycol or mixtures thereof; wherein the composition includes only materials that are considered GRAS or food additive ingredients. The compositions developed for sanitation application onto inanimate equipment and environments are such that they are removed prior to producing product while the compositions for processing aide application directly onto foods are such that they may be removed or remain on the food. When the respective additive packet is mixed into approved base materials (for example: potable water, cleaning detergents, quaternary ammonium sanitizers or antimicrobial food decontamination processing aides) the resulting composition of the solutions have an improved function and can be quantitatively measured under ultraviolet light. The utility of the resulting compositions in this embodiment is that they can be applied to improve sanitation and food processing aide systems while providing a means to measure performance on the surface of inanimate equipment or foods.

One aspect of the invention is to provide sanitarians and inspectors in the food, feed, beverage and pharmaceutical industry with a food grade method that can be used to verify cleaning processes and validate the sanitary design of equipment used for raw and ready to eat foods, animal feed and ingested or topical pharmaceuticals. The sanitation utility of this intervention is that the composition(s) allow sanitarians responsible for cleaning equipment or environments to accomplish two important goals. First; to determine if organic residue on equipment or niches in which the current embodiment composition has attached have been properly removed or cleaned. And the second goal: to verify the removal of the embodiment composition after final rinsing of processing equipment by determining the presence or absence of fluorescence or residual absorption in the ultraviolet spectrum throughout the respective processing equipment. Inspection is performed by measuring the presence or absence of fluorescence post cleaning whereby the presence of unique fluorescence and/or spectroscopy caused as a result of the presence of the composition on the surface or in a dismantled niche indicates that the cleaning procedures were deficient. Such a discovery justifies modification/improvement of the cleaning procedure, the detergent formula; re-design of the equipment, more frequent cleaning or a more effective intervention to prevent unhygienic conditions. The value of the invented composition in sanitation is realized when the invented products are applied onto equipment during the cleaning steps whereby the improved solutions spread over an increased area due to the reduced surface tension enabling the solution to better spread across and penetrate polar and non polar surfaces. The composition includes an emulsifier that increases the adherence onto organic matter and into niches. The fluorescent GRAS or food additive ingredient compositions have been shown by the authors of the current embodiment to attach to organic material particles and settle into niches thus providing a means to evaluate the performance of cleaning procedures by evaluating the equipment for particles and or areas of fluorescence under ultraviolet light at the end of the final cleaning and rinse steps to determine cleaning effectiveness. The invention also serves a useful purpose when added to detergents or sanitizers that must be completely removed prior to food or pharmaceutical production. The presence (ppm) of the fluorescent tracer(s) in the embodiment composition including quaternary sanitizer solution was shown by the authors to be rapidly detected at 1 ppm under ultraviolet light and via a spectrometer. Thus, the utility invention provides novel products to be used to evaluate the performance of cleaning procedures and the sanitary design of the equipment.

Another aspect of the invented composition is to improve the functionality of food decontamination processing aides. The Food and Drug Administration's (FDA) regulations (21 CFR 101.100 (a) (3) (ii)), define processing aides as: a) Substances that are added to a food during the processing of such food but are removed in some manner from the food before it is packaged in its finished form, b) Substances that are added to a food during processing, are converted into constituents normally present in the food, and do not significantly increase the amount of the constituents naturally found in food and c) Substances that are added to a food for their technical or functional effect in the processing but are present in the finished food at insignificant levels and do not have any technical or functional effect in that food.

The current embodiment utilizes a unique combination of GRAS or food additive substances that comply with the FDA's definition of a processing aide and thus can be used alone or mixed in to existing processing aides. Food grade (GRAS) emulsifiers and or surface active agents are key components of the utility invention composition that improves coverage and adherence of the resulting composition and or antimicrobial solution. One of the benefits of adding emulsifiers such as mono and diglycerides or surfactants such as sodium lauryl sulfate or lauric arginate to base food decontamination/antimicrobial processing aides is a noticeable improvement in adherence of the composition to the food surface and an increased coverage of the composition on the surface of the food target. This discovery of improved adherence and coverage is measurable due to the fluorescent components in the composition. The invented composition was shown by the inventors to increase the adherence to the surfaces of meats and produce whereby repeated experiments showed decreased run-off, increase the surface coverage and increased contact time. In addition, it is the opinion of the authors that decreasing the run-off and improving the adherence and contact time should improved the effectiveness of the respective processing aide. Another aspect of the utility invention composition is the addition of synergistic fluorescent food grade additives that provide food safety professionals with a practical and scientific solution to measure the performance of processing aide delivery systems and thus the adequacy of coverage of respective antimicrobial interventions applied directly onto the surfaces of foods. It should be noted that although adding surfactants and emulsifiers increases the performance of processing aides, the fluorescent components may be added to antimicrobial base materials with or without the utility of such components in order to test the performance of such delivery systems. When the entire fluorescent food grade additive packet including food grade emulsifiers is mixed with an approved antimicrobial base material the resulting product show improved coverage and adherence when applied directly onto targeted foods and the coverage can be measured to determine adequacy by visual evaluation of the treated food under ultraviolet light. When only the food grade fluorescent additive portion of the invention is added to an antimicrobial base material the performance of the delivery system can be quantitatively measured under ultraviolet light. Thus when the utility invention substances are mixed into existing antimicrobial processing aides there is an improvement in the overall functionality and effectiveness. Moreover, the invention allows for novel techniques using ultraviolet fluorescence to evaluate the performance of antimicrobial delivery systems with regard to adequacy of food surface coverage.

These and other features, aspects and advantages of the present invention will become better understood with reference to the following drawings, description and claims.

BRIEF DESCRIPTION OF THE DRAWINGS

FIG. 3 provides a flowchart of the present composition invention showing the utility as applied to a cleaning process.

DETAILED DESCRIPTION OF THE INVENTION

Figure 1:
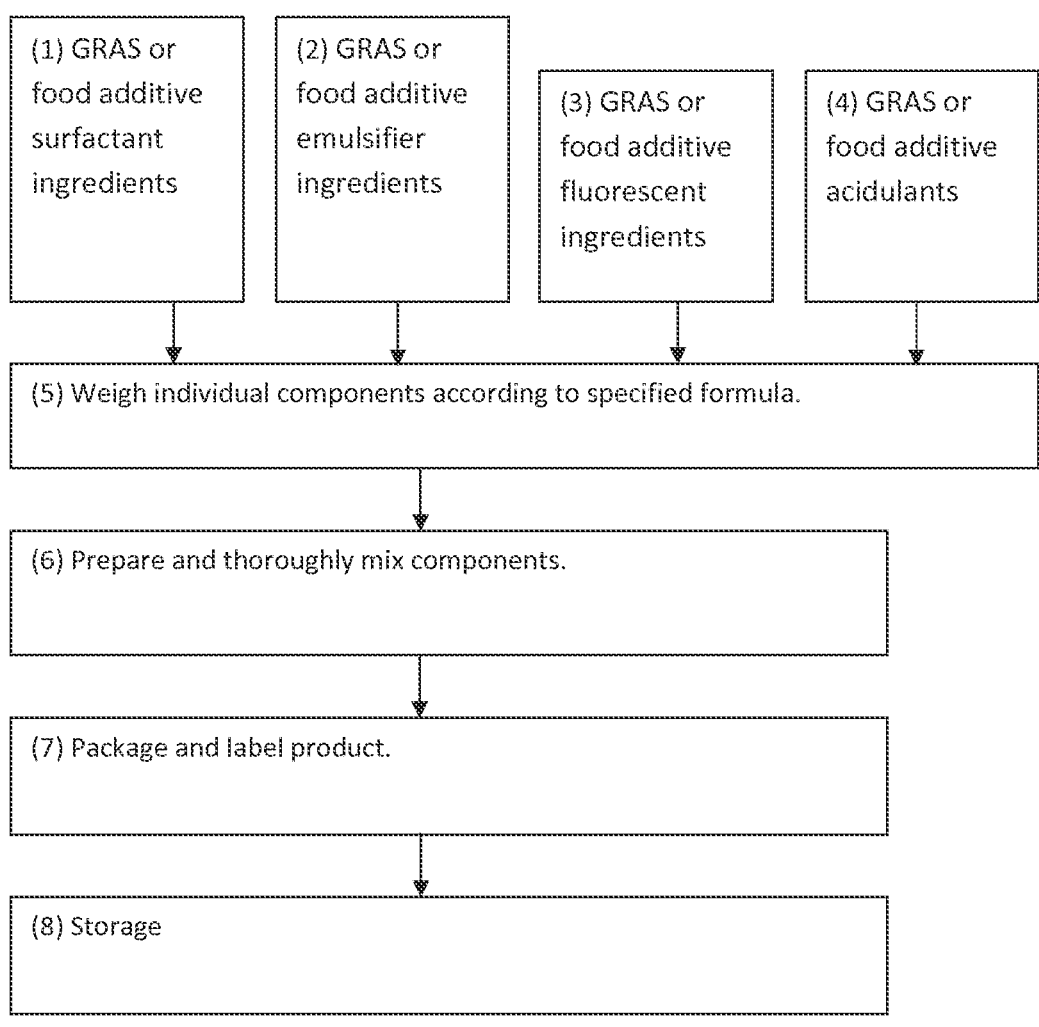
FIG. 1 provides a flowchart of the process for making the dry mix version of the composition invention additive packet.

The following detailed description represents the best currently contemplated modes for carrying out the invention. The description is not to be taken in a limited sense, but is made merely for the purposes of illustrating the general principles of the invention.

Incorporation of compositions revealed in this embodiment into base materials used in sanitation and processing aide antimicrobial agents creates a utility that enhances the functionality of the base materials in which added via improved coverage, penetration and adherence of the respective base material(s). In addition, the compositions in this embodiment allow techniques to quantify the presence/ absence of the composition a) on equipment, b) in niches, c) on food surfaces or d) on the surface of treated food were developed.

Example 1

The current inventors tested the use of Sodium Lauryl Sulfate (STEPANOL® WA-100 NF/USP) and Glyceryl Laurate (Colonial Monolaurin—Ultra-Pure Glyceryl Laurate) to increase the coverage and penetration of component solutions applied to processing equipment in which the solution is removed from food, feed or pharmaceutical contact surfaces prior to production. Glyceryl Laurate and a mixture of propylene glycol and ethyl-W-lawoyl-L-arginate hydrochloride (A&B Ingredients CytoGuard LA) was used by the inventors for applications associated with direct food contact and was shown to increase coverage and adherence/ contact time. Food grade Riboflavin, Folic Acid and Quinine were selected from the many fluorphores available because they were shown to have synergy for the purpose of the tracer concept of the invention.

All three tracer substances Riboflavin, Folic Acid and Quinine have unique molecular structures that enable them to mix into base solutions with varying polar and non polar charges. Studies by the authors of the current embodiment have also shown that the substances show an affinity for organic matter residue (e.g. proteins, fats, oils, soil, mineral deposits, etc.). Riboflavin (B2),Folic Acid (B9) and Quinine are approved food additives (Codex General Standard for Food Additives, Codex STAN 192; Code of Federal Regulations Title 21 Sec. 184.1695; Sec. 73.450; Sec. 104.20, Sec. 101.9 and Sec. 172.575). Riboflavin, Folic Acid and Quinine have a synergistic chemistry allowing them to attach to organic material and settle into niches. Experiments by the inventors have shown that when Riboflavin and Quinine are combined in solution the two GRAS or food additive fluorophores fluoresce synergistically under long and short wave ultraviolet light.

TABLE 1

| Visible Fluorescence Under Short (254 nm) and Long (360 nm) Ultraviolet Light | | | |
|---|---|---|---|
| Visual Fluorescence | 50 ppm Quinine Sulfate, Dihydrate, USP in distilled water | 50 ppm Riboflavin USP in distilled water | 50 ppm Quinine Sulfate, Dihydrate, USP and 50 ppm Riboflavin USP in distilled water |
| Short Wave (254 nm) | Slight | Very Slight | Moderate |
| Long Wave (360 nm) | Moderate | Moderate | Abundant |

Fluorescence was visually measured in dark while exciting the sample via Short and Long Wave Ultraviolet Light from 9 watt Way Too Cool Model WTC 9ML 110 at 6 inches.

Example 2

Very low concentrations of Riboflavin and Folic Acid mixtures can be detected by visible fluorescence and spectroscopy (Table 2 and Table 3).

TABLE 2

Transmission, Absorption (360 nm) and Fluorescence
of Riboflavin (B2) and Folic Acid (B9) in Neutral
and Acidic Distilled Water Solutions.

|  | Distilled Water | 0.5 ppm Riboflavin and 0.5 ppm Folic Acid in Distilled Water | Distilled Water | 0.5 ppm Riboflavin and 0.5 ppm Folic Acid in Distilled Water |
|---|---|---|---|---|
| pH | 7.53 | 7.84 | 3.95 | 3.83 |
| Transmission | 100 | 89.7 | 100 | 89.0 |
| Absorption | 0 | 0.047 | 0 | 0.51 |
| Concentration | 0 | 0.05 | 0 | 0.05 |
| Fluorescence | Void | Slight+ | Void | Slight |

Transmission, Absorption and Concentration measured at 360 nm on Milton Roy Spec 21D at 360 nm on High Intensity. Fluorescence was visually measured in dark while exciting the sample via Mid and Long Wave Ultraviolet Light from 9 watt Way Too Cool Model WTC 9ML 110 at 6 inches. The pH was lowered by adding DL-Tartaric Acid, 99%.

TABLE 3

Transmission, Absorption (360 nm) and Fluorescence of Quaternary
Ammonia (Quat) Base Material containing invented composition.

|  | Potable Water | 300 ppm Quat/Water | 300 ppm Quat plus Invention. | 9 ppm Quat | 9 ppm Quat plus Invention. |
|---|---|---|---|---|---|
| Transmission | 100 | 99.7 | 0.7 | 100 | 35.3 |
| Absorption | 0 | 0.001 | MAXIMUM (>199) | 0 | 0.453 |
| Concentration | 0 | 0.0 | MAXIMUM | 0 | 0.95 |
| Fluorescence | Void | Void | Abundant | Void | Moderate |

Transmission, Absorption and Concentration measured at 360 nm on Milton Roy Spec 21D at 360 nm on High Intensity. Fluorescence was visually measured in dark while exciting the sample via Mid and Long Wave Ultraviolet Light from 9 watt Way Too Cool Model WTC 9ML 110 at 6 inches. The pH was lowered by adding DL-Tartaric Acid, 99%. At 9 ppm Quat Invention = 15 ppm B2, 6 ppm B9, 15 ppm Surfactant, 9 ppm Emulsifier, 22 ppm Acidifier.

The addition of GRAS Riboflavin and Folic Acid in distilled water or quaternary sanitizer has been shown by the authors to produce a novel and measurable composition for detection of base material and tracer presence/absence. Studies have shown that when the GRAS additives are mixed into quaternary ammonia sanitizer the resulting composition is measurable to a greater level of sensitivity than is capable with rapid quat test strips. This is important when all the base material must be removed from processing equipment.

One method of detecting the presence of the food grade vitamin tracer(s) is by exciting the mixture, treated area or sample swab with ultraviolet light so that the vitamins fluoresce. Riboflavin fluorescence is the identifier for visual observations. Folic Acid fluoresces, but not in the visible spectrum. The color of light is related to the wavelength or frequency of the light. Visible light—to which our eyes are most sensitive—falls in the wavelength range of about 400 to 750 nm. In the absence of visible light and when Riboflavin is excited by long-wave ultraviolet light (maximum lambda=~365 nm-below the visible spectrum) Riboflavin emits/fluoresces light waves in the visible spectrum (~450 to 650) which are very distinguishable in the dark when the only other light source is from long (~365 nm) and midrange (~312 nm) ultraviolet light. This phenomenon enables visible detection of Riboflavin at levels as low as 1 ppm. It is well know that different compounds have unique absorption and transmission spectra. Another method of quantifying the presence of the food grade vitamin tracers Riboflavin and Folic Acid is by use of a spectrophotometer whereby wavelength absorption and transmission results of known tracers Vs control samples provide characteristic spectra analysis that can be used to determine the absence or presence with sensitivity down to 1 ppm.

FIG. 1 shows the steps involved with making the composition of the dry mix composition referred to as a "traceable additive packet". The dry mix composition was developed so it can be mixed with a given base material at a later date. As with all the components in the current embodiment, Certificates of Analysis including the CAS number are required for each lot to assure the additive is Food/Pharmaceutical grade. The first steps are to verify COAs for all components. Referring to FIG. 1: The preferred GRAS or food additive surfactant (1) in this invention composition is Sodium Lauryl Sulfate formulated to be 1,000 to 20,000 ppm at the point of use; the preferred GRAS or food additive emulsifier (2) in this invention is the glyceride fatty acid derivative Glycerol Monolaurate formulated to be 500 to 20,000 ppm at the point of use; the preferred fluorescent GRAS or food additives (3) in the composition of this invention include Riboflavin formulated for 100 to 1000 ppm at point of use, Folic Acid formulated for 50 to 500 ppm at point of use and Quinine formulated for 80 to 500 ppm at point of use; the preferred GRAS or food additive (4) acidulate components in this invention includes Citric Acid, Tartaric Acid and Fumaric Acid. The actual composition and ratios of the dry mix components will vary depending on the application and base material. Embodiment formulas applied to inanimate equipment and environments in which the components will be removed prior to production may use higher concentrations of the components than embodiment formulas applied directly to food(s) in which maximum limits are set by FDA or USDA. It must be realized however, that all formulas must comply with EPA and OSHA regulations at the point of use. Embodiment components in formulas applied directly to food(s) must comply with the FDA definition of a processing aide. These mentioned components are listed while other similar food grade additives or components could be used by someone familiar with the art.

The composition form of the traceable additive package can be a dry mixture of the additives or it can be a liquid mixture of the additives in concentrated or ready to use form. The amounts of each additive component shall be specified for intended use. The amount of each food grade additives in the fluorescent additive packages that are to be mixed with the base materials will vary depending on the volume of base material to be mixed into.

Each individual dry component is weighed 5, separately in order to achieve defined ratios for formulas developed specifically for the base material and application. Components are prepared and thoroughly mixed 6, bulk components shall be prepared for mixing by de-clumping, grinding or other means to reduce the particles sizes to facilitate thorough mixing. Each component is mixed thoroughly to disperse all constituents uniformly throughout the dry mix batch. After mixing, portions of the finished batch are packaged and labeled according to regulatory requirements and shall include use instructions 7. After packaging the products are stored in a dry cool location (8).

Figure 2:
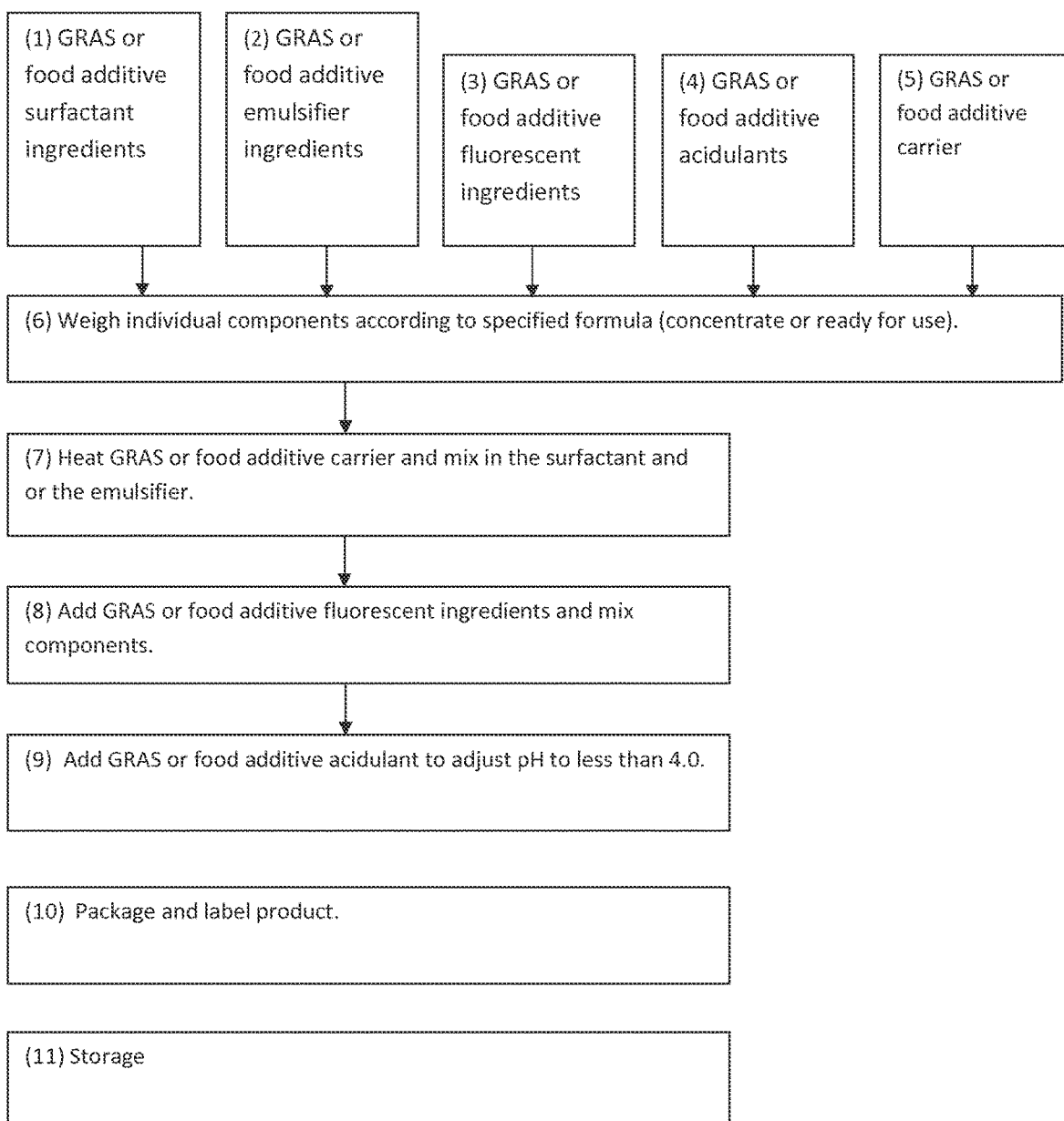
FIG. 2 provides a flowchart of the process for making the hydrated version of the composition invention.

FIG. 2 is a flow chart showing the process for making the hydrated version of the embodiment composition. The process is the same as that for the dry packets with the exception that a GRAS or food additive carrier is included as a component and the hydrated composition is to be used with or without a base material is stored in a concentrated or ready to use form. Components 1, 2, 3, 4, 5 are weighed 6, per set formulas to achieve the desired composition for the specific base material and application. For concentrated compositions of the embodiment, the GRAS or food additive surfactant (1) and or the GRAS or food grade emulsifier (2) should be mixed first into a heated GRAS or food additive carrier such as water, propylene glycol or glycerin. After the GRAS or food additive carrier, surfactant and or emulsifier are thoroughly mixed 7, the GRAS or food additive fluorescent component(s) are added and thoroughly mixed into the solution 8. The next step is to add GRAS or food additive acidulant (9) to adjust the pH of the composition to less than 4. Experiments by the authors have shown that fluorescence from the embodiment components is stable at pH ranges from 1 to 7. The authors have chosen less than pH 4 in order to inhibit outgrowth of microorganisms in the embodiment solution during storage. The preferred pH range for the composition prior to mixing with base material is pH 1 to 3. After mixing and before packaging each batch should be tested for pH, fluorescence, absorption and transmission according to specified parameters. In specification finished batches are packaged, labeled (10), and stored (11) at ambient temperature.

FIG. 3 is a flow chart showing how the GRAS or food additive composition is mixed with sanitizer(s) or cleaning chemical(s) for visualization of cleaning efficacy so those trained in the art can validate or verify the hygienic condition of equipment or environments after cleaning. The steps involved with making the combined fluorescent additive and base material invention solution include; (1) select the base material and the specific volume that will be used for the application. It is important to know the composition of the base material, its physical properties and establish a set volume. For purposes of this embodiment, base material can be potable water or any of the various sanitation chemicals that has been approved for use in the food, beverage, pharmaceutical, feed industry by appropriate regulatory authorities. The base material will be approximately 95% of the total end product. Potable tap water is an excellent base material for combining with the embodiment composition to produce a solution that can be applied to equipment at any stage of the cleaning process prior final rinse. Quat sanitizers, liquid soaps and detergents have also been shown by the authors to be excellent base materials. Riboflavin mixed easily into solution when 1,000 ppm was added to KayQuat II (>1,000 ppm quaternary ammonia). Fluorescence was intense from day one through day 270 and has not diminished at the time of this publication. Similar tests were performed on Ajax Liquid Soap with Bleach Alternative with similar results.

It should be noted that bench top studies with concentrate hypochlorite solutions have been shown by the authors to rapidly quench Riboflavin fluorescence. Slight fluorescence was observed for up to 4 hours when 2,500 ppm Riboflavin was added to a 30% solution of chlorine bleach and fluorescence was diminished completely after 8 hours. Highly alkaline ammonia base material produced similar results. The authors were concerned that chlorinated alkaline detergents and/or foaming cleaners would quench the fluorescence of the embodiment composition so tests were performed to determine the effect.

Example 3

Tests were performed on two stainless steel meat tenderizer rollers. The tenderizer knife rollers are made of 48 circular knives with ¼ inch circular spacers in between the blades. At each blade spacer junction there is a micro niche.

Two formula compositions in potable water base material were compared for performance, one with and one without surfactant or emulsifier. Formula 1 contained 750 ppm Riboflavin, 300 ppm Folic Acid as fluorescent tracers, 750 ppm of the surfactant Sodium Lauryl Sulfate, 1,500 ppm of the acidulate Citric Acid Monohydrate and 750 ppm of the emulsifier Glycerol Monolaurate (Monolaurin) in potable water base material. Formula 2 contained 750 ppm Riboflavin, 300 ppm Folic Acid as fluorescent tracers and 1,500 ppm Citric Acid Monohydrate in potable water but did not contain Sodium Lauryl Sulfate or Monolaurin. Approximately 30 lbs of raw beef cutlets were made on the tenderizer each day of the tests. The tenderizer parts were labeled part 1 and part 2. The parts were both thoroughly rinsed with potable water to remove visible meat residue. Part 1 was treated with formula 1 and part 2 was treated with formula 2. The parts were thoroughly foamed with Kay Chlorinated Foamer (SODIUM HYPOCHLORITE 2%, SODIUM HYDROXIDE 1%, SODIUM CARBONATE 5-20% and COCAMINE OXIDE 1-5%). The chlorinated foamer was left on the treated knife roller parts for approximately 10 minutes and thoroughly rinsed off. The parts were evaluated under ultraviolet light (365 nm) A) after rinsing-before foaming with a chlorinated alkaline cleaner, B) after foaming and rinsing off the foam after ~10 minutes and C) after scrubbing and rinsing. The tests were repeated on different days and the tenderizer knife rollers randomized. Both formulas resulted in fluorescence from the embodiment composition remaining clearly visible in the niches of the tenderizer parts, on the blades and in some of the rinse water droplets under the parts upon inspection post cleaning with the chlorinated detergent.

The composition including a GRAS or food additive surfactant and emulsifier consistently showed a higher percentage of fluorescent blade/spacer junctions and the chlorinated foamer used did not significantly decrease the ability to visualize the fluorescence in the niches. Results are presented in table 4.

TABLE 4

| Meat Tenderizer % Blade Spacers Showing Fluorescence under Long Wave Ultraviolet Light | | | | |
|---|---|---|---|---|
| Formula | Day | Post Rinse Pre Foam | Post Foam & Rinse | Post Scrub & Rinse |
| 1 | 1 | 62.5% | 52.1% | 10.4% |
| 2 | 1 | 41.7% | 41.7% | 14.6% |
| 1 | 2 | 60.4% | 60.4% | 12.5% |
| 2 | 2 | 58.3% | 52.1% | 18.8% |
| 1 | 3 | 50% | 47.9% | 16.7 |
| 2 | 3 | 45.8% | 37.5% | 14.6% |
| 1 | 4 | 70.8% | 72.9% | 20.8% |
| 2 | 4 | 52.1% | 47.9% | 18.8% |

Formula 1 = Potable water plus 750 ppm Riboflavin, 300 ppm Folic Acid, 750 ppm Sodium Lauryl Sulfate, 1,500 ppm Citric Acid Monohydrate and 750 ppm Glycerol Monolaurate (Monolaurin).
Formula 2 = Potable water plus 750 ppm Riboflavin, 300 ppm Folic Acid, 1,500 ppm Citric Acid Monohydrate.

The authors have shown that the formulation pH range of the hydrated embodiment has been shown effective with regard to fluorescence between pH 1 and 7. However, a caution to consider when combining an acid to a chlorinated solution containing hypochlorite is the potential for chlorine gas production. Chlorine gas and water combine to make hydrochloric and hypochlorous acids in solution. It is important to note that the specific amounts of the individual constituents in the intended composition and the base material must be known in order to calculate the amount and concentration of each constituent in the final product. The pH of the final product should also be quantified and adjustments made to the composition to achieve the desired outcome for safety and utility. Although trials by the authors have not revealed problems with irritation from chlorine gas when mixing the fluorescent additive composition which contains acidifier(s) with chlorine sanitizer or chlorinated foaming detergents, authors recommend controlled bench top trials under a ventilated hood if strong alkaline or chlorinated base materials are to be used in order to determine the safety, half life and intensity of tracer fluorescence prior to use in a plant.

From FIG. 3, select the appropriate embodiment composition 2, for the base material. The authors have developed and evaluated various formulas with regard to components, ratios and performance. Tests have shown the optimal composition for cleaning assessments to include Riboflavin, Quinine mixed into a solution of Sodium Lauryl Sulfate and Monolaurin dissolved in Propylene Glycol whereby the composition pH is reduced to less than 4 using Citric Acid. The composition can be mixed with water or remain in concentrated form until time of use whereby it can be mixed into water or other approved base materials at the appropriate ratios to end up with the desired ppm of each component at the point of use.

Example 4

Tests by the authors comparing an acidified formula to a non acidified formula applied to a retail meat grinder auger showed the formula with a low pH identified unclean surfaces better than the formula that was at a neutral pH. Sections of the auger sprayed with the acidified formula fluoresced brighter than sections sprayed with the non acidified formula. Upon closer inspection and during the re-cleaning process very thin layers (almost transparent) of either mineral deposits from the cleanup water, or protein and fat from grinding beef, or a mixture of the three were determined to have fluorescent tracer attached after treatment with the invention. This investigator cannot be certain of the composition of the thin layers of fluorescent material on some sections of the auger. However, it has been observed that the formula containing Riboflavin, Folic Acid, Sodium Lauryl Sulfate, Monolaurin and Citric Acid adhered to the thin layers and fluoresced greater than the formulas without the surfactant, emulsifier or the acidifier. The test was repeated on 3 different cleaning cycles with similar results each trial.

It could be hypothesized that the surfactant and emulsifier components in the formula reduces the surface tension and allows the fluorescent solution to better penetrate and spread into niches while the acidifier lowers the pH of the solution facilitating an interaction with food or mineral residue. The acidifier may also buffer the high pH of chlorinated alkaline cleaning solutions.

It is very easy to change the ratio of components to fit the base material for optimal performance and least cost. For example a base material such as potable water that does not contain surfactants or acidifiers would require a fluorescent additive packet formula with a higher surfactant and acidifier percentage compared to a base material such as a soap that already contains an adequate amount of surfactants but requires an acidifier to achieve the desired results. Knowing the ingredients and the pH of the base material is very important. It should go without saying that the volume or weight of the base material is very important in order to add the correct amount of the fluorescent additive packet to meet the end product minimum fluorescent additive concentrations for adequate penetration, spreading, adherence, stability and detection.

Example 5

An additional fluorescent training formula was developed to be used for sanitation employee training. The training formula resulted in a product that can be sprayed onto all equipment surfaces prior to cleaning. The addition of rice starch enables the product to adhere to all equipment surfaces regardless if they clean or unclean or have niches for the fluorescent tracers to attach or settle into. The least cost training formula contained 15,000 ppm modified rice starch (Remygel 652 FG-P) and 100 ppm Riboflavin mixed in warm potable water. The solution was sprayed onto and into a stainless steel HOBART retail meat grinder prior to cleaning with a chlorinated alkaline detergent and rinsing with potable water. When the grinder was inspected under normal lighting post clean and rinse, the test solution was slightly visible in some sections. When the same grinder was inspected using a portable long wave (365 nm) ultraviolet light (UVP ML-49) there were more than double the areas that showed that the starch/Riboflavin solution had not been removed.

From FIG. 3, once the component materials are weighed out and ready to blend 3, thoroughly mix the fluorescent additive package components with the base material. The base material will comprise the significant majority of the volume of the resulting solution. When mixing the fluorescent additive package contents with a base material it is important to dissolve or disperse the relatively small amount of additives into the base solution. This can be accomplished by dissolving or diluting the additive packet contents into hot water prior to mixing into the base material. Another method for mixing the fluorescent additives into the base material is to use of a metering pump that introduces known amounts of the fluorescent additive solution into the stream of the base material. It should be noted that the additives selected for the fluorescent additive packets were chosen due to their food grade status and solubility. In addition, the components used in the current invention are capable of withstanding boiling water without losing their functionality with regard to their utility according to the embodiment.

Methods for thoroughly mixing the embodiment components into solution are dependent on the base material properties, volume and the type of container used for mixing. For a small container such as a 24 ounce plastic spray bottle, the appropriate fluorescent additive packet can simply be poured into the empty spray bottle first and the base material added on top of the mixture. After the correct amount of base material is in the spray bottle, the bottle is capped and vigorously shaken until the additives are in solution. For a larger container such as a drum or bulk tank, a high speed agitator or re-circulating pump may be used.

It is advised to sample the mixed solution and test it for fluorescence, absorption and transmission prior to use. The pH target should be based on application and in the range of 1.5 to 7.0 for optimal fluorescence under long (360-365 nm).

Apply the combined solution 4, to the equipment or environment that will be cleaned and evaluated can be accomplished in a number of ways. On a small scale such as the spray bottle example used above, the invention may be hand sprayed onto processing equipment. On a larger scale the invention could be supplied through a centralized system with sanitation hose drops in the various areas of the processing plant that allow employees to spray the invention onto the equipment and environment prior to cleaning. The invention could also be contained in a portable pressurized tank equipped with a spray hose that could be transported throughout the plant. The invention could be applied to equipment through a clean in place system or via spray bars. Regardless of the method for application, the concept is that invention should be applied so that it has an opportunity to come in contact with soil and to work its way into hard to reach, hard to clean areas and potential niches. Thus, adequate volumes and time of application are required. In addition, depending on the process and equipment complexity, the application may be most effective while the equipment is running or after sections of the equipment have been removed for access.

Example 6

Table 5 shows results from a trial performed by one of the authors that revealed the utility of combining visual and swab evaluations. Equipment in a Retail Meat Market was treated with the fluorescent invention packet that was mixed into potable water and sprayed onto the equipment prior to cleaning. After cleaning the equipment was inspected using a portable long wave UV light (UVP ML-49). In addition, the equipment was swabbed using one ply tissue KemWipes. Fluorescence inspection of the equipment occurred in the dimly lit processing area. Inspection of the KimWipe swabs occurred in a dark room. The equipment was re-cleaned and re-sampled. Results indicated the utility of swabbing equipment (i.e. the grinder motor shaft) that cannot be evaluated in a dark room.

TABLE 5

Visual Fluorescence via Long wave Ultraviolet Light - Treatment Formula 1,000 ppm Riboflavin and Potable Water

| Equipment Parts | Equipment/ Swab Fluorescence Pre Clean | Equipment/ Swab Fluorescence Post Clean 1 | Equipment/ Swab Fluorescence Post Clean 2 | Equipment/ Swab Fluorescence Post Clean 2 |
|---|---|---|---|---|
| Grinder/ Auger | Abundant/ Abundant | None/None | None/None | NA |
| Auger Seal | Abundant/ Abundant | Slight/Slight | None/None | NA |
| Grinder motor Shaft | Moderate/ Abundant | None/Moderate | None/None | NA |
| Tenderizer | Abundant/ Moderate | Moderate/ Moderate | Slight/Slight | Slight/Very Slight |
| Table Top | Abundant/ Abundant | None/None | NA | NA |

The cleaning of the treated equipment or environment 5, can occur immediately after application. One of the objectives for using the invention is to verify that the standard cleaning procedures performed on a daily basis are in fact effective. Therefore, the typical cleaning procedures should be performed using the same chemicals, water pressure, water temperature, physical agitation, flow rate, dwell time etc. 6, inspection and analysis to quantify the presence or absence of fluorescent additive(s) remaining on the equipment or environment can occur at any stage of the cleaning procedure. However, for purposes of this example inspection and analysis will be described for a piece of equipment after the final cleaning step and after it has passed routine visual pre-operative inspection. As previously discussed and illustrated, there are several ways to quantify the presence or absence of residual fluorescent additive tracer left on the equipment or its parts. One method is to use a portable long wave ultraviolet (UV) light in a dark or dimly lit room. For excitation of Riboflavin and Quinine resulting in fluorescence it is essential to use a long wave UV light, not only a short wave UV light. Long wave UV lights with higher watts that emit specific 360-365 nm UV light waves produce the best results when Riboflavin is used alone. For Riboflavin and Quinine solutions, the combination long wave (365 nm) and short wave (254 nm) is the light source combination that excites Riboflavin and Quinine synergistically. The darker the surroundings of the equipment being inspected for fluorescence the better since trace amounts of fluorescent residual is more evident when excited by long wave UV light in the absence of visible light. If the area to be inspected cannot be darkened, then parts of the equipment can be placed on a cart or carried into a darker area for long wave UV light inspection. The person performing the inspection should hold the UV light close (~10 inches) to the points on the equipment being inspected. An inspector trained in the art of inspecting equipment for cleanliness should use similar techniques for inspecting the equipment for tracer fluorescence. The addition of Folic Acid to the composition provides utility when assessing removal of cleaning chemicals by analyzing the rinsate. Such a method is to use potable water and perform rinse tests whereby parts of the equipment are rinsed with potable water and the rinsate collected for analysis. This is an especially effective method for closed systems that are cleaned in place (CIP). For other systems, potable rinse water can be sprayed onto the inspected area and the rinsate collected. The rinsate can be collected in containers or by collecting on absorbent materials such as sponges or Kemwipes. The rinsate can be analyzed for fluorescence by shining the long wave UV light onto the sample in a dark room or small long wave UV box or enclosure. In addition, the rinsate can be analyzed via a spectrophotometer for unique absorption and transmission as was presented in Tables 1 and 2. Another method is to aseptically swab the equipment sample point with a sanitary sample sponge, KemWipe or other sanitary swab that can be analyzed under long wave UV light in a dark room or small long wave UV box or enclosure that blocks out visible light waves. In addition, the sample swabs may be processed by adding to deionized water and stomached to extract fluorescent tracer residue that may be present. The water extract can be analyzed via spectroscopy to determine the presence or absence of unique absorption or transmission caused by the fluorescent tracer additives.

Example 7

In addition to using a swab technique to determine if the fluorescent additives have been removed from processing equipment, a technique referred to as a rinse test can also be a useful method. Trials were performed on a raw retail meat grinder and a ready to eat retail deli slicer to quantify the presence or absence of the tracer solution pre and post cleaning. Rinse water was collected as it ran off of the equipment at different stages and analyzed on a Milton Roy Spec 21D at 360 nm High Intensity. Samples were also visually evaluated under long and midrange UV light in a dark room. Results from spectroscopy and visual evaluation under UV light clearly indicated that the initial rinse water post treatment contained the tracer solution. When rinsate was collected after thorough cleaning the spectroscopy and UV results were not significantly different than the potable water control.

From FIG. 3, inspection and analysis results 7, should be documented and reported for each piece of equipment.

Reports from the investigation and analysis that show no fluorescence, transmission or absorption unique to the fluorescent additive tracer indicate that the equipment sanitary design and cleaning procedures are valid to maintain hygienic conditions. However, if inspection and analysis post cleaning show the presence of unique fluorescence, transmission or absorption then the cleaning procedures for the respective equipment are not valid and need improvement. Areas that showed presence of fluorescent additive are considered unclean and shall be re-cleaned and re-inspected until clean. The process of re-cleaning 8, should continue until inspection results indicate that there is no unique fluorescence, absorption or transmission caused by the fluorescent additive tracer. Cleaning procedures and the sanitary design of the equipment shall be re-assessed and modified until acceptable results are common practice 9, for all areas that failed the inspection or analysis. For example, if fluorescence was observed between a delron wear strip that was bolted onto the stainless steel frame of a food transport conveyor belt there is a chance that bacteria could harbor in the same niche that cannot be properly accessed for cleaning between the delron strip and the frame. If the standard cleaning procedure did not specify removal of the wear strip for proper cleaning, then either the cleaning procedures must be modified to assure that the sanitation personnel have the proper tools to remove the strip for proper cleaning; or the equipment must be re-designed so that the harborage point is eliminated or so the wear strip can be removed without special tools. Sanitarians or engineers trained in the art should be able to determine the best method for the particular process and equipment.

Figure 4:
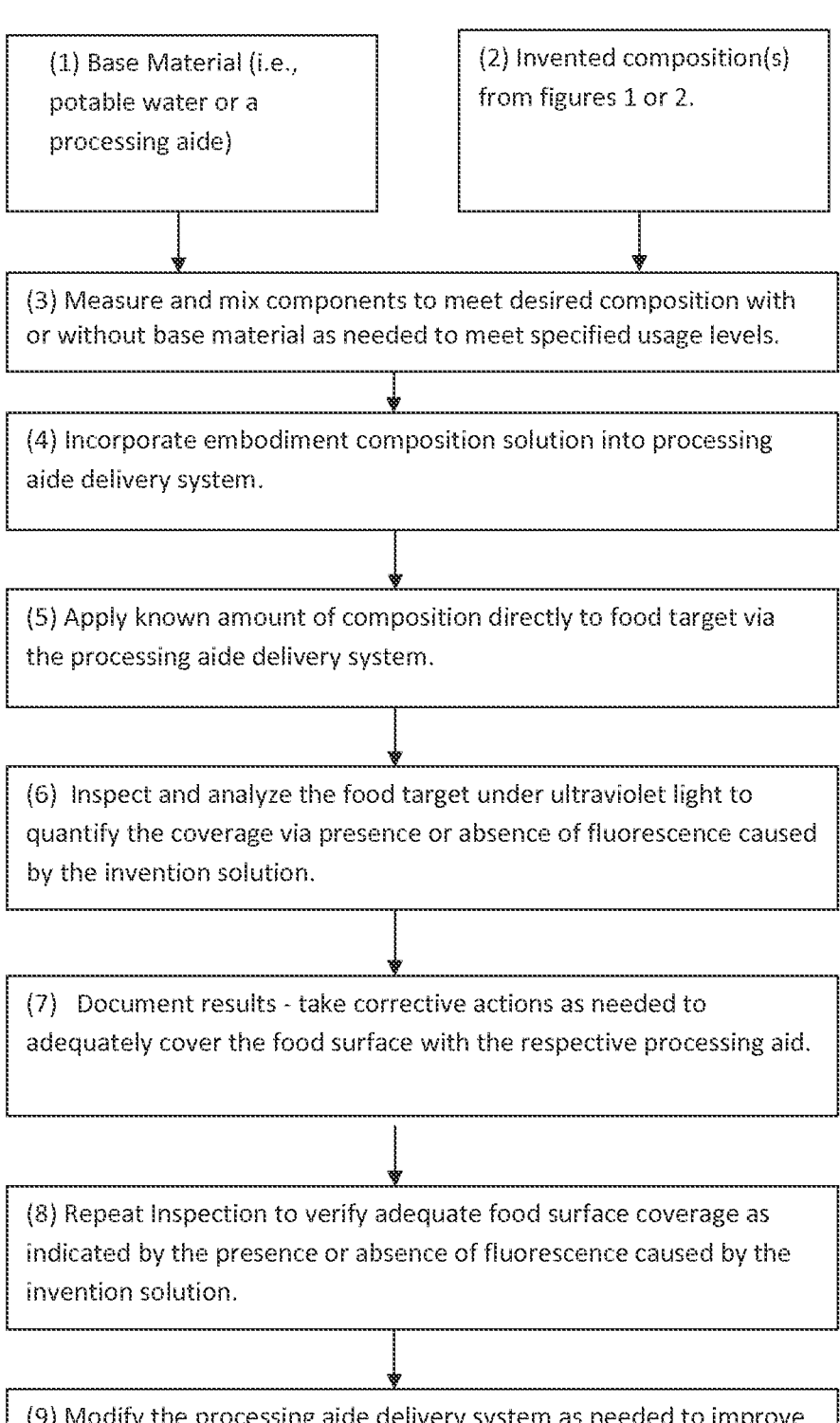
FIG. 4 provides a flowchart of the present composition invention showing the applied directly onto a food via a processing aide application.

FIG. 4. Illustrates the steps involved with making a fluorescent antimicrobial solution, applying it directly to food(s), analyzing the foods for coverage adequacy and re-assessing the process as needed. The FDA definition for processing aides must be complied with. It must berealized that compositions including base materials approved for use on inanimate equipment for the most part are not appropriate for direct food contact. Many of the fluorescent invention formulas used for sanitation application whereby the additive solutions are removed from the food contact surfaces prior to production are not appropriate for direct food application. It should be noted however that several of the key components in the current embodiment were selected because they are actually naturally occurring in many of the foods that the invention is intended to be applied. Components in the current embodiment such as Riboflavin, Folic Acid, Quinine, Citric Acid, Tartaric Acid, Ascorbic Acid, Fumaric Acid, Lauric Arginate, Glycerol Monolaurate (Monolaurin) and other similar Generally Recognized as Safe additives are approved up to specific parts per million in foods and beverages either without being labeled or provided they are on the food or beverage label. For these reasons, the selection of the composition components or processing aide formula is dependent on the specific application. Step 1, is to formulate the respective embodiment composition to be mixed in with the food grade base material. It is important to first determine the food regulations pertaining to the specific food and country for which the food is to be consumed before deciding to use the invention. For example, Lauramide arginine ethyl ester (LAE) common name Lauric Arginate is a cationic surfactant that is approved for direct food contact. Mono and di-glycerides (Monolaurin) are GRAS emulsifiers that are approved for direct food contact. Monolaurin (a monoglyceride) is a key ingredient in the invention because it acts as an emulsifier to facilitate spreading and adherence of the invention solution to fats and oils.

Processing aides have different approved usages, allowable active ingredient levels and labeling requirements. Some processing aides are approved for use on certain foods and not others. Some processing aide solutions are approved for use in some countries and not others. It is equally important to determine the respective food regulations for use and labeling of the embodiment components as food additives. An example of a good resource for approved food additives is the United States is the Office of Food Additive Safety (HFS-200) Center for Food Safety and Applied Nutrition-Food And Drug Administration-5100 Paint Branch Parkway College Park, MD 20740-3835-Phone: (240) 402-1200. Another example of a good reference for use of food additives is the Joint FAO/WHO Expert Committee on Food Additives (JECFA) an international expert scientific committee that is administered jointly by the Food and Agriculture Organization of the United Nations (FAO) and the World Health Organization (WHO). For example, a list of approved added Riboflavin levels by food category can be found in the CODEX GENERAL STANDARD FOR FOOD ADDITIVES (GSFA) PROVISIONS FOR RIBO-FLAVINS.

According to the present intervention, once the approved food grade antimicrobial base material and food grade fluorescent composition formula components approved usage and labeling requirements have been determined, the next step is to obtain Letters of Guarantee and Certificates of Analysis from the suppliers of the respective processing aides, food grade vitamins and other food grade additives intended for use in the end composition to be applied to the food.

Deciding to use a dry or hydrated 1, version (concentrated or ready for use) of the embodiment product is dependent on the application, capability of the end user, storage and shipping cost factors.

There are many base material choices for processing aides 2, that have been approved in 21 Code of Federal Regulations (CFR) for use as food additives, generally recognized as safe (GRAS) notices and pre-market notifications, and approved in letters conveying acceptability determinations for direct food contact in the food industry. Examples include but are not limited to Lauric Arginate (LAE), Lactoferrin, Peroxyacetic Acid, Octanoic Acid, Hydrogen Peroxide, Peroxyoctanoic Acid, 1-Hydroxyethylidene-1,1-Diphosphonic Acid (HEDP), Organic Acids (i.e., Lactic, Acetic, and Citric Acid). See Antimicrobials In Foods by P. Michael Davidson, John Nikolas Sofos and Alfred Larry Branen.

Formulas incorporating the embodiment components must be must be developed to comply with regulatory requirements and be approved prior to use. It is very important to determine the allowable additive and antimicrobial base material active ingredient that can be applied directly on or in specific foods. The factors to consider are the concentration of the additives/antimicrobial active ingredients, the interaction effect and the total amount of the combined solution that is added to the food. The concentration is a function of the formula while the weight gain or amount of the solution picked up on the food is a function of the delivery system.

Once the formula is developed and approved for use, the food grade fluorescent additive packet components and the antimicrobial base materials are measured/weighed 3, to meet the specified formula. Mixing of the components with potable water or the antimicrobial intervention base material 4, can be accomplished in batches by adding a known amount of components additive(s) directly into the water or antimicrobial solution and mixing it with a high speed blender. Another method for mixing the composition additives into water or the antimicrobial base material is to use of a metering pump that introduces known amounts of the fluorescent additive solution into the stream of the base material solution. The objective of mixing is to disperse the embodiment components/additive ingredients homogeneously throughout the water or antimicrobial base material solution that will be applied directly onto the target foods.

Example 8

The mixed compositions fluorescent additives and base material solutions can be stored for later use or applied immediately. Studies by the authors have shown the fluorescence stability of the base formulas to last for long periods of time.

TABLE 6

Riboflavin (B2), Folic Acid (B9) Fluorescence
Stability @ 500 ppm B2 and 100 ppm B9

| Antimicrobial Base Material | pH | Fluorescence October 2011 | Fluorescence January 2012 | Fluorescence June 2012 |
|---|---|---|---|---|
| Lactic Acid | 1.2 | Abundant | Moderate+ | Moderate+ |
| Lactic Acid Plus | 1.0 | Abundant | Moderate+ | Moderate+ |
| Beefxide | 1.6 | NA | Abundant | Abundant |
| Pera Tec (15% Peroxyacetic Acid, 6% Hydrogen Peroxide) | 2.9 | Moderate+ | Moderate+ | Moderate– |
| Cytoguard (LAE) | 3.2 | Abundant | Moderate+ | Moderate+ |

Fluorescence visually evaluated via Mid and Long Wave Ultraviolet Light from 9 watt Way Too Cool Model WTC 9ML 110 at 6 inches. Fluorescence Scale from Most to Least = Abundant +, 0, –: Moderate +, 0, –: Slight +, 0, – and Void.

During food production 5, the formulated embodiment solution is applied directly onto the target food(s). For example, by pumping it from a batch container to a spraying system or the invention solution can be put in a pressurized tank and delivered to spray nozzles that apply the invention solution directly onto the food. Spray nozzles applying the embodiment processing aide could be located in spray cabinets or over and under conveyor belts carrying food products. Some spray systems are inside slicers whereby the antimicrobial solution is sprayed directly onto the food as it is being sliced. Other systems use a waterfall, a flume or moat to drench the products with the antimicrobial solution. There are a number of innovative intervention systems that apply antimicrobial solutions directly onto various types of foods. One of the key factors is to know how much of the fluorescent invention solution is retained on or in the targeted food to assure the regulated maximum limits are not exceeded. Another key factor is that the intervention delivery system should be capable of adequately covering the entire surface of the targeted food. It should be noted that one of the discoveries during the research by the authors was that the addition of Monolaurin and or Sodium Lauryl Sulfate to various processing aide base materials and water greatly increased the coverage and adherence. This discovery was only made possible by the fluorescence provided by Riboflavin and Quinine combined in solution.

Inspection and analysis to assure adequate coverage of the intervention solution containing fluorescent additives 6, can be accomplished by shining long wave and/or midrange and/or short wave ultraviolet lights onto the treated food surface depending on the fluorophore components and their respective synergy. The preferred method for this embodiment is to use the long wave UV light waves (~365-390 nm) which excite Riboflavin molecules which fluoresce wavelengths (420-600 nm) in the visible spectrum that can be seen by the human eye during inspection. There are a number of ways to accomplish the inspection via UV light. For example, treated foods can be inspected with a portable ultraviolet (UV) light in a dark or dimly lit room. Fluorescence from food treated with the embodiment can also be seen in ambient lighting conditions if the UV light source is held very close to the food being inspected. Results are dependent on the quality of the UV light, the wattage and the concentration of the fluorescent component on the food. It should be noted that Riboflavin fluorescence is more evident when excited by higher watt UV light (peak 365 nm) in the absence of visible light. The person performing the inspection should hold the UV light close (~4 to 10 inches) to the food samples being inspected. If the area to be inspected cannot be darkened, then samples of the food can be taken to a darker area for UV analysis or the food sample could be placed into a small enclosure that blocks visible light while inspecting. Surface area grids can be used to quantify the coverage area. Acceptable food safety limits can be established for the minimum surface area requirement and maximum number of defective units.

Example 9

Bench top tests on produce and beef surface fat were performed where 500 ppm Riboflavin was added to several different antimicrobial base materials. The Riboflavin/Base Material solutions were applied directly to whole vine tomatoes. Tomatoes studies showed that fluorescent Cytoguard (Lauric Arginate) and Per Tec (Peroxy Acetic Acid and Hydrogen Peroxide) stayed on the tomato surface significantly longer than Lactic Acid or Lactic Acid Plus which did not appear to adhere to the tomato skin. Fluorescent Lactic Acids drained off of the tomatoes within 3 to 5 seconds whereas Cytoguard and Pera Tec adhered to tomato surfaces for minutes. This is an interesting result in light of the need for adherence in order to have time to inspect the foods after they pass through an intervention system. All of the fluorescent antimicrobials did adhere to the area of the fruit where the stem is attached. In another set of studies, honeydew melons, watermelons, cantaloupes and tomatoes were treated with a formulation composition including Monolaurin and Sodium Lauryl and a formulation composition without Monolaurin and Sodium Lauryl Sulfate. Both formulas included 500 ppm of Riboflavin. The formula containing the GRAS emulsifier and surfactant was made by dissolving them in propylene glycol prior to incorporating the Riboflavin and water. The final composition of formula 1 was 1,000 ppm Monolaurin, 1,000 ppm Sodium Lauryl Sulfate, 500 ppm Riboflavin in 3% lactic acid and water solution. Formula 2 contained 500 ppm in a 3% lactic acid solution. Results showed that formula 2 without Monolaurin and Sodium Lauryl Sulfate had very slight adherence to the surfaces of the honeydew melon or the water melon or the tomato. While formula 1 results showed 90 to 100% coverage and adherence to all three produce surfaces. Results from the cantaloupe test showed no significant difference in coverage or adherence between the two formulas.

Tests on strips of beef surface fat showed excellent results for all tests. The 500 ppm Riboflavin antimicrobial solutions were poured onto the beef fat samples which were inspected under UV light in a dark area. The fluorescent antimicrobial solutions appeared to absorb into the beef fat tissue and fluoresced Moderate to Moderate+. The test was repeated months later using the same solutions in order to test the stability of the solutions with regard to Riboflavin fluorescence. The beef fat samples were suspended vertically and each solution was applied onto the samples using a disposable pipette. Results were very similar to the previous study. The fluorescent solutions absorbed into the fat tissue. As the solutions dripped down with gravity they left fluorescent traces wherever they touched.

Tests were performed on raw chilled beef (Top Sirloin Sub Primal) and skin on (Whole Broiler Chicken) and skin off (Boneless Chicken Breast) chilled poultry to determine the effect of adding Monolaurin (food grade Glyceryl Laurate-mono glyceride) to Riboflavin and Folic Acid in 4 different pathogen intervention solutions. The compositions were mixed by simply adding the dry Riboflavin, Folic Acid and ground Monolaurin into the processing aide base materials. It should be noted that not all of the Monolaurin went into solution as indicated by wavy precipitate remaining in the bottom of the spray bottles. Two different formulas for each intervention were equally sprayed (~5 sprays) onto the beef or chicken and measured under UV light. Tables 7, 8 and 9 present results which show the addition of Monolaurin (ML) significantly improved coverage percent for Lactic Acid and Beefxide applied to chilled beef surface fat and skin on chilled poultry.

TABLE 7

Raw Chilled Beef Intervention Coverage on Surface Fat - 1,000 ppm Riboflavin and 200 ppm Folic Acid with and without 1,000 ppm Monolaurin (Glyceryl Laurate)

| Antimicrobial Base Material | pH | Coverage with ML | Fluorescence with ML | Coverage without ML | Fluorescence without ML |
|---|---|---|---|---|---|
| 2.5% Lactic Acid (Purac FCC 88) | 2.79 | 89% | Moderate | 64% | Moderate+ |
| 5% CytoGuard LA (A&B Ingredients) | 7.02 | 95% | Moderate | 85% | Moderate+ |
| 2.5% Beefxide (Birko) | 2.9 | 90% | Moderate | 70% | Abundant |
| 5% CytoGuard LA (A&B Ingredients) plus Citric Acid | 2.79 | 97% | Moderate | 90% | Abundant– |

Coverage measured visually from video tape analysis using a grid as a reference. Fluorescence Scale from Most to Least = Abundant +, 0, –: Moderate +, 0, –: Slight +, 0, – and Void.

TABLE 8

Raw Skin on Chicken Intervention Coverage - 1,000 ppm Riboflavin and 200 ppm Folic Acid with and without 1,000 ppm Monolaurin (Glyceryl Laurate)

| Antimicrobial Base Material | pH | Coverage with ML | Fluorescence with ML | Coverage without ML | Fluorescence without ML |
|---|---|---|---|---|---|
| 2.5% Lactic Acid (Purac FCC 88) | 2.79 | 95% | Abundant– | 80% | Abundant |
| 5% CytoGuard LA (A&B Ingredients) | 7.02 | 100% | Abundant– | 100% | Abundant |
| 2.5% Beefxide (Birko) | 2.9 | 90% | Abundant– | 80% | Abundant |

TABLE 8-continued

Raw Skin on Chicken Intervention Coverage - 1,000 ppm Riboflavin and 200 ppm Folic Acid with and without 1,000 ppm Monolaurin (Glyceryl Laurate)

| Antimicrobial Base Material | pH | Coverage with ML | Fluorescence with ML | Coverage without ML | Fluorescence without ML |
|---|---|---|---|---|---|
| 5% CytoGuard LA (A&B Ingredients) plus Citric Acid | 2.79 | 100% | Abundant– | 100% | Abundant |

Coverage measured visually from video tape analysis using a grid as a reference. Fluorescence Scale from Most to Least = Abundant +, 0, –: Moderate +, 0, –: Slight +, 0, – and Void.

TABLE 9

Raw Skin off Chicken Breast Intervention Coverage - 1,000 ppm Riboflavin and 200 ppm Folic Acid with and without 1,000 ppm Monolaurin (Glyceryl Laurate)

| Antimicrobial Base Material | pH | Coverage with ML | Fluorescence with ML | Coverage without ML | Fluorescence without ML |
|---|---|---|---|---|---|
| 2.5% Lactic Acid (Purac FCC 88) | 2.79 | 100% | Abundant+ | 100% | Abundant |
| 5% CytoGuard LA (A&B Ingredients) | 7.02 | 100% | Abundant | 100% | Abundant |
| 2.5% Beefxide (Birko) | 2.9 | 100% | Abundant | 100% | Abundant |
| 5% CytoGuard LA (A&B Ingredients) plus Citric Acid | 2.79 | 100% | Abundant | 100% | Abundant |

Coverage measured visually from video tape analysis using a grid as a reference. Fluorescence Scale from Most to Least = Abundant +, 0, –: Moderate +, 0, –: Slight +, 0, – and Void.

These tests indicate the utility of using the fluorescent composition to determine coverage and adherence. The tests also show the improvement in surface coverage when the GRAS or food additive emulsifier Monolaurin is added to the processing aide base material. Processing aides such as those typically used in the beef industry intervention sprays (i.e. Organic Acid Sprays) could benefit from this embodiment. The utility of a composition including Riboflavin and Monolaurin is great because both are naturally occurring in beef. The application of an improved processing aide with visualization qualities could provide an ongoing food safety improvement for the industry. For example, Beef trim is routinely sampled for *E. coli* O157:H7 testing. The trim sampling protocol is to excise surface samples (N60/10,000 lbs). The protocol is to excise the surface because the surface of the carcass is where the pathogen contaminates the meat, typically from the hide, fecal or ingesta, not on the interior of the meat. If the invention was used whereby the antimicrobial organic acid carcass spray contained the fluorescent additive solution then the excised surface samples collected for *E. coli* O157:H7 testing could be placed under UV light and inspected to verify carcass coverage. Data could be collected and statistics calculated to determine if there was a correlation between lack of coverage and positive *E. coli* O157:H7 trim samples. This could be an ongoing verification procedure that could provide valuable feedback to operations and engineering.

Poultry processors use antimicrobial interventions to control *Salmonella* and *Campylobacter* which are hazards likely to occur in raw poultry. Adequate coverage is important to the effectiveness of the interventions. Monolaurin added to Lactic Acid improved the coverage and adherence of the composition and the Riboflavin/Folic Acid tracers allow coverage to be measured. An inspector trained in the art of inspecting food surfaces for defects should use similar techniques for inspecting the food surfaces for tracer fluorescence. In addition, food surface samples may be processed by extracting the water components from the food surface in order to analyze for absorption and transmission.

Example 10

Studies by the authors have also shown that the fluorescent antimicrobial applied to beef trimming can be identified after the trimmings are ground and formed into patties. Tests were conducted at a retail meat market whereby custom grinds were produced for research. Fresh bench trim was sprayed with a 500 ppm Riboflavin and Cytoguard solution. Four tenths of a pound of the fluorescent antimicrobial solution was sprayed onto ten pounds of beef trim. Trim fluoresced when inspected under long wave UV light. The trim was ground twice through a $1/8^{th}$ inch plate and patties were formed. Patties were inspected under visible and long wave UV light. Under visible light there was no perceptible difference in appearance vs. control. Under long wave UV light Riboflavin fluorescence was obvious as it was observed scattered throughout the ground beef patties. Patties were frozen and evaluated at month 3 and month 6. Riboflavin fluorescence was detected at both 3 and 6 months with scores of moderate fluorescence.

Inspection and analysis results 7, should be documented and corrective actions implemented as needed to improve the food safety systems. Specific times, stages in the process, locations on the food target etc, where fluorescence, unique absorption or transmission was absent must be quantified and considered as an intervention system failure. Foods or sections of the food targets that do not show presence of antimicrobial fluorescent additive solution are considered at risk and 8, should be re-treated with the antimicrobial solution and re-inspected. The process of re-treating should be closely monitored to avoid exceeding the regulatory limits for antimicrobial or fluorescent additives.

Failed inspection results shall be reported to and utilized by plant management to modify the intervention processes as needed to improve the food safety system(s). Passing inspection results shall be reported to and utilized by plant management to verify and validate that the intervention systems are operating as designed.

Example 11

Studies by a third party microbiology lab have shown that the embodiment formulas exhibit and improve antimicrobial properties (Table 10). Enriched samples of *Listeria monocytogenes* and *Salmonella* (Controls) were treated with embodiment formulas developed for point of use application. Formula 1 was comprised of Sodium Lauryl Sulfate (1,000 ppm), Monolaurin/Glyceryl Laurate (1,000 ppm) and Riboflavin (500 ppm) blended into potable water and acidified to pH 2.8 with Citric Acid Monohydrate. Formula 2 was comprised of Sodium Lauryl Sulfate (1,000 ppm), Monolaurin/Glyceryl Laurate (1,000 ppm) and Riboflavin (500 ppm) blended into an approved quaternary ammonium (300 ppm) sanitizer/disinfectant base material. Formula 3 was the same as formula 2 with the addition of 100 ppm Folic Add, Formula 3 was tested on a different day which explains the different control inoculums levels.

Results show log reductions for all formulas tested with the greatest log reductions occurring when 300 ppm quat sanitizer was used as the base material.

TABLE 10

Comparative log reductions of *Listeria monocytogenes* (LM) and *Salmonella* (SAL) treated with embodiment processing aide solutions.

| | Log LM Recovered/ LM Log Reduction | Log SAL Recovered/ SAL Log Reduction |
|---|---|---|
| 15 second | | |
| Control | 6.3/0.0 | 6.3/0.0 |
| Formula 1 | 4.0/2.3 | 6.1/1.7 |
| Formula 2 | 1.3/5.0 | 0.8/5.5 |
| Control | 5.8/0.0 | 5.6/0.0 |
| Formula 3 | <2.0/3.8 | <2.0/3.6 |
| 10 minutes | | |
| Control | 7.8/0.0 | 7.8/0.0 |
| Formula 1 | 2.5/5.3 | 2.0/5.8 |
| Formula 2 | 2.5/5.3 | 2.0/5.8 |
| Control | 5.8/0.0 | 5.8/0.0 |
| Formula 3 | <2.0/3.8 | <2.0/3.6 |

Example 12

Concentrated embodiment formulas were developed to be diluted at the point of use. Studies by a third party microbiology lab have shown that the embodiment formulas exhibit and improve the performance of existing antimicrobials. Enriched samples of *Listeria monocytogenes, E. coli* O157:H7 and *Candida* (Controls) were treated with 2 different embodiment formulas (1 & 2) and one commercial food processing aide. Formula 1 was a concentrated mixture of Sodium Lauryl Sulfate (20,000 ppm), Monolaurin/Glyceryl Laurate (20,000 ppm) and Riboflavin (500 ppm) blended into Propylene Glycol and acidified to pH 2.5 with Citric Acid Monohydrate. Formula 2 was Sodium Lauryl Sulfate (20,000 ppm), Monolaurin/Glyceryl Laurate (20,000 ppm) and Riboflavin (500 ppm) blended into a commercial antimicrobial processing aide containing Lauric Arginate (LAE) base solution and adjusted to a pH of 2.2 using Citric Acid Monohydrate. The commercial processing aide (LAE) was also tested without modification. All formulas were diluted (1 part mixture to 20 parts water) to achieve 5% solutions at the point of use. Formulas were challenged into known *Listeria monocytogenes* (LM), *E. coli* O157:H7 (O157) and *Candida* (CAN) inoculums and log reductions measured at 15 seconds and 10 minutes.

Results presented in Table 11 show that formulas 1 and 2 reduced LM by more than 2.5 logs (36,100%) at 15 seconds of contact. After 10 minutes of contact formula 1 had reduced LM by 4.3 logs and formula 2 by 5.2 logs. Both embodiment formulas reduced LM more than the commercial antimicrobial food processing aide (LAE Base) which only reduced LM by 1.1 and 1.6 logs at 15 seconds and 10 minutes respectively. At 15 seconds, *E. coli* O157:H7 reduction was similar for formula 1 and LAE Base (1.4 log) while formula 2 showed a 2.1 reduction. After 10 minutes formula 2 showed a much greater log reduction (5.8) compared to formula 1 and LAE Base (1.7). Formula 2 also outperformed formula 1 and LAE for log reduction of *Candida* at 15 seconds and 10 minutes showing a very significant comparative decrease ($10^{1.9}$ or a 79 times).

TABLE 11

Comparative log reductions of *Listeria monocytogenes* (LM), *E. coli* O157:H7 (O157) and *Candida* (CAN) treated with 5% processing aide solutions.

|  | Log LM Recovered/LM Log Reduction | Log O157 Recovered/O157 Log Reduction | Log CAN Recovered/CAN Log Reduction |
|---|---|---|---|
| 15 second |  |  |  |
| Control | 7.1/0.0 | 6.8/0.0 | 6.1/0.0 |
| Formula 1 | 4.5/2.6 | 5.4/1.4 | 5.2/0.9 |
| LAE Base | 6.0/1.1 | 5.4/1.4 | 5.5/0.6 |
| Formula 2 | 4.6/2.5 | 4.7/2.1 | 3.6/2.5 |
| 10 minutes |  |  |  |
| Control | 7.2/0.0 | 6.8/0.0 | 6.0/0.0 |
| Formula 1 | 2.9/4.3 | 5.1/1.7 | 4.8/1.2 |
| LAE Base | 5.6/1.6 | 5.1/1.7 | 4.8/1.2 |
| Formula 2 | 2.0/5.2 | 1.0/5.8 | 2.9/3.1 |

Example 13

Formulas were tested to determine log reduction differences when embodiment GRAS additive solutions of Sodium Lauryl Sulfate, Monolaurin/Glyceryl Laurate and Riboflavin were added to Lactic Acid. An approved commercial lactic acid solution designed to be diluted 1 part to 40 parts water was used as a base solution. Formula 1 was comprised of 20,000 ppm Sodium Lauryl Sulfate, 20,000 ppm Monolaurin and 500 ppm Riboflavin blended into a 90% Lactic Acid/10% Propylene Glycol solution. Formula 2 had 30,000 ppm Monolaurin/Glyceryl Laurate and 500 ppm Riboflavin blended into a 90% Lactic Acid/10% Propylene Glycol solution. The Lactic Acid base and the 2 embodiment formulas were diluted 1 part to 40 parts water to achieve a 2.5% solution at the point of use. Enriched *Listeria monocytogenes* (LM) and *E. coli* O157:H7 (O157) samples were treated with the 3 different solutions and results measured after 15 seconds and 10 minutes.

Results (Table 12) indicated that LM reduction was greatest at 15 seconds when treated with 2.5% Lactic Acid base without Sodium Lauryl Sulfate, Riboflavin and/or Monolaurin/Glyceryl Laurate. At 10 minutes the LM log reductions were similar for all three solutions. *E. coli* O157:H7 reduction at 15 seconds was greater for the 2.5% embodiment test formulas 1 & 2 compared to the 2.5% Lactic Acid base. However at 10 minutes, the 2.5% Lactic Acid and 2.5% Formula 1 solutions both produced 6.1 log reductions. Formula 2 produced a 4.8 log reduction.

TABLE 12

Comparative log reduction of *Listeria monocytogenes* (LM) and *E. coli* O157:H7 (O157) treated with 2.5% processing aide solutions.

|  | Log LM Recovered/Reduced | Log O157 Recovered/Reduced |
|---|---|---|
| 15 second |  |  |
| Control | 7.0/0.0 | 7.1/0.0 |
| Lactic Acid Base | 2.0/5.0 | 6.9/0.2 |
| Formula 1 | 5.1/1.9 | 1.5/5.6 |
| Formula 2 | 6.3/0.7 | 3.6/3.5 |

TABLE 12-continued

Comparative log reduction of *Listeria monocytogenes* (LM) and *E. coli* O157:H7 (O157) treated with 2.5% processing aide solutions.

|  | Log LM Recovered/Reduced | Log O157 Recovered/Reduced |
|---|---|---|
| 10 minutes |  |  |
| Control | 7.0/0.0 | 7.1/0.0 |
| Lactic Acid Base | 1.6/5.4 | 1.0/6.1 |
| Formula 1 | 1.0/6.0 | 1.0/6.1 |
| Formula 2 | 1.9/5.1 | 2.3/4.8 |

The forgoing summary, detailed description, and examples provide a basis for understanding the invention. Since the invention can comprise a variety of embodiments, the above information is not intended to be limiting. It will become apparent to those trained in the art that modifications and variations may be made without deviating from the scope and spirit of the present invention as described and claimed.

What is claimed is:

1. A method of processing a food, an animal hide or a hard surface comprising:

applying a composition to a surface of the food, the animal hide or the hard surface to form a treated surface;

visually inspecting the treated surface under ultraviolet light to detect fluorescence on a portion of the treated surface where contamination remains;

after the applying and visually inspecting steps, rinsing the treated surface with water;

cleaning the portion of the treated surface where the contamination was detected;

reapplying the composition to the portion of the treated surface where the contamination was detected; and repeating the visually inspecting, rinsing, cleaning, and reapplying steps until no fluorescence is detected on the treated surface, the composition comprising glycerol monolaurate; riboflavin; citric acid or salt thereof; and water; wherein the composition is a solution having a pH ranging from 1 to 7, and the ratio of glycerol monolaurate to riboflavin ranges from 1:2 to 200:1;

wherein the composition, when applied to the surface of the food, the animal hide, or the hard surface in an amount containing from 1 ppm to 100 ppm riboflavin, has greater adherence to the surface and covers a greater area of the surface than the same amount of the same composition which does not contain glycerol monolaurate; and wherein the composition adheres to the contamination and fluoresces under ultraviolet light after rinsing the treated surface with water.

2. The method of claim 1 further comprising the step of applying the composition to a portion of the exterior surface of the food or the animal hide if fluorescence was not detected on that portion of the exterior surface.

3. The method of claim 1 wherein the method is used in processing food and the food comprises meat, poultry, fruit, or a vegetable.

4. The method of claim 1 wherein the composition is applied to the exterior surface of the food by spray, waterfall drench, flume drench, or moat drench.

5. The method of claim 4 wherein the pH ranges from 1 to 4.

6. The method of claim 1 further comprising a cationic surfactant.

7. The method of claim 6 wherein the cationic surfactant comprises lauric arginate.

8. The method of claim 1 further comprising folic acid in a ratio of the glycerol monolaurate to folic acid ranging from 1:1 to 400:1.

9. The method of claim 1 further comprising quinine in a ratio of glycerol monolaurate to quinine ranging from 1:1 to 250:1.

10. The method of claim 1 further comprising a cleaning agent.

11. The method of claim 10 wherein the cleaning agent is a liquid soap, a detergent, a quaternary ammonium sanitizer, or a chlorinated alkaline compound.

12. A method of cleaning a hard metal surface comprising:

applying a composition to the hard metal surface to form a treated surface;

visually inspecting the treated surface under ultraviolet light to detect fluorescence on a portion of the treated surface where contamination remains;

rinsing the treated surface with water;

cleaning the portion of the treated surface where the contamination was detected;

reapplying the composition to the portion of the treated surface if where the contamination was detected; and repeating the visually inspecting, rinsing, cleaning, and reapplying steps until no fluorescence is detected on the treated surface, wherein the composition comprises glycerol monolaurate; riboflavin; citric acid or salt thereof; and water; the composition being a solution having a pH ranging from 1 to 7, and the ratio of glycerol monolaurate to riboflavin ranging from 1:2 to 200:1;

wherein the composition, when applied to the hard metal surface in an amount containing from 1 ppm to 100 ppm riboflavin, has greater adherence to the surface and covers a greater area of the surface than the same amount of the same composition which does not contain glycerol monolaurate; and wherein the composition adheres to the contamination and fluoresces under ultraviolet light after rinsing the treated surface with water.

* * * * *